United States Patent
Koop et al.

(10) Patent No.: US 10,994,145 B2
(45) Date of Patent: May 4, 2021

(54) IMPLANTABLE CARDIAC MONITOR

(71) Applicant: CARDIAC PACEMAKERS, INC., St. Paul, MN (US)

(72) Inventors: Brendan Early Koop, Ham Lake, MN (US); Lance Eric Juffer, Lino Lakes, MN (US); Michael J. Kane, St. Paul, MN (US); Benjamin J. Haasl, Forest Lake, MN (US); Keith R. Maile, New Brighton, MN (US); Arthur J. Foster, Blaine, MN (US)

(73) Assignee: CARDIAC PACEMAKERS, INC., St. Paul, MN (US)

( * ) Notice: Subject to any disclaimer, the term of this patent is extended or adjusted under 35 U.S.C. 154(b) by 147 days.

(21) Appl. No.: 15/710,464

(22) Filed: Sep. 20, 2017

(65) Prior Publication Data
US 2018/0078771 A1 Mar. 22, 2018

Related U.S. Application Data

(60) Provisional application No. 62/397,894, filed on Sep. 21, 2016.

(51) Int. Cl.
*A61N 1/37* (2006.01)
*A61B 5/00* (2006.01)
(Continued)

(52) U.S. Cl.
CPC .............. *A61N 1/37* (2013.01); *A61B 5/0028* (2013.01); *A61B 5/0031* (2013.01);
(Continued)

(58) Field of Classification Search
CPC ............ A61B 2562/162; A61B 5/0028; A61B 5/0031; A61B 5/0402; A61B 5/0422;
(Continued)

(56) References Cited

U.S. PATENT DOCUMENTS

| 3,835,864 A | 9/1974 | Rasor et al. |
| 3,943,936 A | 3/1976 | Rasor et al. |

(Continued)

FOREIGN PATENT DOCUMENTS

| AU | 2008279789 B2 | 1/2009 |
| AU | 2008329620 B2 | 5/2014 |

(Continued)

OTHER PUBLICATIONS

US 8,886,318 B2, 11/2014, Jacobson et al. (withdrawn)
(Continued)

*Primary Examiner* — Scott M. Getzow
*Assistant Examiner* — Vynn V Huh
(74) *Attorney, Agent, or Firm* — Seager, Tufte & Wickhem LLP.

(57) ABSTRACT

An implantable cardiac monitor (ICM) may be configured to be deployed subcutaneous, submuscular, or substernal at a position that enables the ICM to detect cardiac activity. In some cases, the ICM includes a housing that includes a body portion and a tail portion. A first electrode may be disposed adjacent a first end of the body portion, a second electrode may be disposed adjacent a second end of the body portion and a third electrode may be disposed adjacent a tail end of the tail portion. A controller may be disposed within the housing and may be operably coupled to the first electrode, the second electrode and the third electrode. The controller may be configured to select a pair of the first electrode, the second electrode and the third electrode to use for sensing cardiac electrical activity and to communicate information about the sensed activity to a second medical device.

19 Claims, 13 Drawing Sheets

(51) Int. Cl.
*A61B 5/07* (2006.01)
*A61B 5/042* (2006.01)
*A61B 5/0452* (2006.01)
*A61N 1/372* (2006.01)
*A61N 1/375* (2006.01)
*A61B 5/0402* (2006.01)

(52) U.S. Cl.
CPC .......... *A61B 5/0422* (2013.01); *A61B 5/0452* (2013.01); *A61B 5/076* (2013.01); *A61B 5/686* (2013.01); *A61B 5/6861* (2013.01); *A61B 5/6869* (2013.01); *A61B 5/6886* (2013.01); *A61N 1/37211* (2013.01); *A61B 5/0402* (2013.01); *A61B 2562/162* (2013.01); *A61N 1/3756* (2013.01)

(58) Field of Classification Search
CPC ....... A61B 5/0452; A61B 5/076; A61B 5/686; A61B 5/6861; A61B 5/6869; A61B 5/6886; A61N 1/37; A61N 1/37211; A61N 1/3756
See application file for complete search history.

(56) References Cited

U.S. PATENT DOCUMENTS

| | | |
|---|---|---|
| 4,142,530 A | 3/1979 | Wittkampf |
| 4,151,513 A | 4/1979 | Menken et al. |
| 4,157,720 A | 6/1979 | Greatbatch |
| RE30,366 E | 8/1980 | Rasor et al. |
| 4,243,045 A | 1/1981 | Maas |
| 4,250,884 A | 2/1981 | Hartlaub et al. |
| 4,256,115 A | 3/1981 | Bilitch |
| 4,263,919 A | 4/1981 | Levin |
| 4,310,000 A | 1/1982 | Lindemans |
| 4,312,354 A | 1/1982 | Walters |
| 4,323,081 A | 4/1982 | Wiebusch |
| 4,357,946 A | 11/1982 | Dutcher et al. |
| 4,365,639 A | 12/1982 | Goldreyer |
| 4,440,173 A | 4/1984 | Hudziak et al. |
| 4,476,868 A | 10/1984 | Thompson |
| 4,522,208 A | 6/1985 | Buffet |
| 4,537,200 A | 8/1985 | Widrow |
| 4,556,063 A | 12/1985 | Thompson et al. |
| 4,562,841 A | 1/1986 | Brockway et al. |
| 4,593,702 A | 6/1986 | Kepski et al. |
| 4,593,955 A | 6/1986 | Leiber |
| 4,630,611 A | 12/1986 | King |
| 4,635,639 A | 1/1987 | Hakala et al. |
| 4,674,508 A | 6/1987 | DeCote |
| 4,712,554 A | 12/1987 | Garson |
| 4,729,376 A | 3/1988 | DeCote |
| 4,754,753 A | 7/1988 | King |
| 4,759,366 A | 7/1988 | Callaghan |
| 4,776,338 A | 10/1988 | Lekholm et al. |
| 4,787,389 A | 11/1988 | Tarjan |
| 4,793,353 A | 12/1988 | Borkan |
| 4,819,662 A | 4/1989 | Heil et al. |
| 4,858,610 A | 8/1989 | Callaghan et al. |
| 4,886,064 A | 12/1989 | Strandberg |
| 4,887,609 A | 12/1989 | Cole |
| 4,928,688 A | 5/1990 | Mower |
| 4,967,746 A | 11/1990 | Vandegriff |
| 4,987,897 A | 1/1991 | Funke |
| 4,989,602 A | 2/1991 | Sholder et al. |
| 5,012,806 A | 5/1991 | De Bellis |
| 5,036,849 A | 8/1991 | Hauck et al. |
| 5,040,534 A | 8/1991 | Mann et al. |
| 5,058,581 A | 10/1991 | Silvian |
| 5,078,134 A | 1/1992 | Heilman et al. |
| 5,109,845 A | 5/1992 | Yuuchi et al. |
| 5,113,859 A | 5/1992 | Funke |
| 5,113,869 A | 5/1992 | Nappholz et al. |
| 5,117,824 A | 6/1992 | Keimel et al. |
| 5,127,401 A | 7/1992 | Grevious et al. |
| 5,133,353 A | 7/1992 | Hauser |
| 5,144,950 A | 9/1992 | Stoop et al. |
| 5,170,784 A | 12/1992 | Ramon et al. |
| 5,179,945 A | 1/1993 | Van Hofwegen et al. |
| 5,193,539 A | 3/1993 | Schulman et al. |
| 5,193,540 A | 3/1993 | Schulman et al. |
| 5,241,961 A | 9/1993 | Henry |
| 5,243,977 A | 9/1993 | Trabucco et al. |
| 5,259,387 A | 11/1993 | DePinto |
| 5,269,326 A | 12/1993 | Verrier |
| 5,284,136 A | 2/1994 | Hauck et al. |
| 5,300,107 A | 4/1994 | Stokes et al. |
| 5,301,677 A | 4/1994 | Hsung |
| 5,305,760 A | 4/1994 | McKown et al. |
| 5,312,439 A | 5/1994 | Loeb |
| 5,313,953 A | 5/1994 | Yomtov et al. |
| 5,314,459 A | 5/1994 | Swanson et al. |
| 5,318,597 A | 6/1994 | Hauck et al. |
| 5,324,316 A | 6/1994 | Schulman et al. |
| 5,331,966 A | 7/1994 | Bennett et al. |
| 5,334,222 A | 8/1994 | Salo et al. |
| 5,342,408 A | 8/1994 | deCoriolis et al. |
| 5,370,667 A | 12/1994 | Alt |
| 5,372,606 A | 12/1994 | Lang et al. |
| 5,376,106 A | 12/1994 | Stahmann et al. |
| 5,383,915 A | 1/1995 | Adams |
| 5,388,578 A | 2/1995 | Yomtov et al. |
| 5,404,877 A | 4/1995 | Nolan et al. |
| 5,405,367 A | 4/1995 | Schulman et al. |
| 5,411,031 A | 5/1995 | Yomtov |
| 5,411,525 A | 5/1995 | Swanson et al. |
| 5,411,535 A | 5/1995 | Fujii et al. |
| 5,456,691 A | 10/1995 | Snell |
| 5,458,622 A | 10/1995 | Alt |
| 5,466,246 A | 11/1995 | Silvian |
| 5,468,254 A | 11/1995 | Hahn et al. |
| 5,472,453 A | 12/1995 | Alt |
| 5,522,866 A | 6/1996 | Fernald |
| 5,540,727 A | 7/1996 | Tockman et al. |
| 5,545,186 A | 8/1996 | Olson et al. |
| 5,545,202 A | 8/1996 | Dahl et al. |
| 5,571,146 A | 11/1996 | Jones et al. |
| 5,591,214 A | 1/1997 | Lu |
| 5,620,466 A | 4/1997 | Haefner et al. |
| 5,634,938 A | 6/1997 | Swanson et al. |
| 5,649,968 A | 7/1997 | Alt et al. |
| 5,662,688 A | 9/1997 | Haefner et al. |
| 5,674,259 A | 10/1997 | Gray |
| 5,683,426 A | 11/1997 | Greenhut et al. |
| 5,683,432 A | 11/1997 | Goedeke et al. |
| 5,706,823 A | 1/1998 | Wodlinger |
| 5,709,215 A | 1/1998 | Perttu et al. |
| 5,720,770 A | 2/1998 | Nappholz et al. |
| 5,728,154 A | 3/1998 | Crossett et al. |
| 5,741,314 A | 4/1998 | Daly et al. |
| 5,741,315 A | 4/1998 | Lee et al. |
| 5,752,976 A | 5/1998 | Duffin et al. |
| 5,752,977 A | 5/1998 | Grevious et al. |
| 5,755,736 A | 5/1998 | Gillberg et al. |
| 5,759,199 A | 6/1998 | Snell et al. |
| 5,774,501 A | 6/1998 | Halpern et al. |
| 5,792,195 A | 8/1998 | Carlson et al. |
| 5,792,202 A | 8/1998 | Rueter |
| 5,792,203 A | 8/1998 | Schroeppel |
| 5,792,205 A | 8/1998 | Alt et al. |
| 5,792,208 A | 8/1998 | Gray |
| 5,814,089 A | 9/1998 | Stokes et al. |
| 5,827,216 A | 10/1998 | Igo et al. |
| 5,836,985 A | 11/1998 | Rostami et al. |
| 5,836,987 A | 11/1998 | Baumann et al. |
| 5,842,977 A | 12/1998 | Lesho et al. |
| 5,855,593 A | 1/1999 | Olson et al. |
| 5,873,894 A | 2/1999 | Vandegriff et al. |
| 5,891,184 A | 4/1999 | Lee et al. |
| 5,897,586 A | 4/1999 | Molina |
| 5,899,876 A | 5/1999 | Flower |
| 5,899,928 A | 5/1999 | Sholder et al. |
| 5,919,214 A | 7/1999 | Ciciarelli et al. |

(56) References Cited

U.S. PATENT DOCUMENTS

| | | |
|---|---|---|
| 5,935,078 A | 8/1999 | Feierbach |
| 5,941,906 A | 8/1999 | Barreras, Sr. et al. |
| 5,944,744 A | 8/1999 | Paul et al. |
| 5,954,757 A | 9/1999 | Gray |
| 5,978,713 A | 11/1999 | Prutchi et al. |
| 5,991,660 A | 11/1999 | Goyal |
| 5,991,661 A | 11/1999 | Park et al. |
| 5,999,848 A | 12/1999 | Gord et al. |
| 5,999,857 A | 12/1999 | Weijand et al. |
| 6,016,445 A | 1/2000 | Baura |
| 6,026,320 A | 2/2000 | Carlson et al. |
| 6,029,085 A | 2/2000 | Olson et al. |
| 6,041,250 A | 3/2000 | DePinto |
| 6,044,298 A | 3/2000 | Salo et al. |
| 6,044,300 A | 3/2000 | Gray |
| 6,055,454 A | 4/2000 | Heemels |
| 6,073,050 A | 6/2000 | Griffith |
| 6,076,016 A | 6/2000 | Feierbach |
| 6,077,236 A | 6/2000 | Cunningham |
| 6,080,187 A | 6/2000 | Alt et al. |
| 6,083,248 A | 7/2000 | Thompson |
| 6,106,551 A | 8/2000 | Crossett et al. |
| 6,115,636 A | 9/2000 | Ryan |
| 6,128,526 A | 10/2000 | Stadler et al. |
| 6,141,581 A | 10/2000 | Olson et al. |
| 6,141,588 A | 10/2000 | Cox et al. |
| 6,141,592 A | 10/2000 | Pauly |
| 6,144,879 A | 11/2000 | Gray |
| 6,162,195 A | 12/2000 | Igo et al. |
| 6,164,284 A | 12/2000 | Schulman et al. |
| 6,167,310 A | 12/2000 | Grevious |
| 6,201,993 B1 | 3/2001 | Kruse et al. |
| 6,208,894 B1 | 3/2001 | Schulman et al. |
| 6,211,799 B1 | 4/2001 | Post et al. |
| 6,221,011 B1 | 4/2001 | Bardy |
| 6,240,316 B1 | 5/2001 | Richmond et al. |
| 6,240,317 B1 | 5/2001 | Villaseca et al. |
| 6,256,534 B1 | 7/2001 | Dahl |
| 6,259,947 B1 | 7/2001 | Olson et al. |
| 6,266,558 B1 | 7/2001 | Gozani et al. |
| 6,266,567 B1 | 7/2001 | Ishikawa et al. |
| 6,270,457 B1 | 8/2001 | Bardy |
| 6,272,377 B1 | 8/2001 | Sweeney et al. |
| 6,273,856 B1 | 8/2001 | Sun et al. |
| 6,277,072 B1 | 8/2001 | Bardy |
| 6,280,380 B1 | 8/2001 | Bardy |
| 6,285,907 B1 | 9/2001 | Kramer et al. |
| 6,292,698 B1 | 9/2001 | Duffin et al. |
| 6,295,473 B1 | 9/2001 | Rosar |
| 6,297,943 B1 | 10/2001 | Carson |
| 6,298,271 B1 | 10/2001 | Weijand |
| 6,307,751 B1 | 10/2001 | Bodony et al. |
| 6,312,378 B1 | 11/2001 | Bardy |
| 6,315,721 B2 | 11/2001 | Schulman et al. |
| 6,336,903 B1 | 1/2002 | Bardy |
| 6,345,202 B2 | 2/2002 | Richmond et al. |
| 6,351,667 B1 | 2/2002 | Godie |
| 6,351,669 B1 | 2/2002 | Hartley et al. |
| 6,353,759 B1 | 3/2002 | Hartley et al. |
| 6,358,203 B2 | 3/2002 | Bardy |
| 6,361,780 B1 | 3/2002 | Ley et al. |
| 6,368,284 B1 | 4/2002 | Bardy |
| 6,371,922 B1 | 4/2002 | Baumann et al. |
| 6,398,728 B1 | 6/2002 | Bardy |
| 6,400,982 B2 | 6/2002 | Sweeney et al. |
| 6,400,990 B1 | 6/2002 | Silvian |
| 6,408,208 B1 | 6/2002 | Sun |
| 6,409,674 B1 | 6/2002 | Brockway et al. |
| 6,411,848 B2 | 6/2002 | Kramer et al. |
| 6,424,865 B1 | 7/2002 | Ding |
| 6,434,429 B1 | 8/2002 | Kraus et al. |
| 6,438,410 B2 | 8/2002 | Hsu et al. |
| 6,438,417 B1 | 8/2002 | Rockwell et al. |
| 6,438,421 B1 | 8/2002 | Stahmann et al. |
| 6,440,066 B1 | 8/2002 | Bardy |
| 6,441,747 B1 | 8/2002 | Khair et al. |
| 6,442,426 B1 | 8/2002 | Kroll |
| 6,442,432 B2 | 8/2002 | Lee |
| 6,443,891 B1 | 9/2002 | Grevious |
| 6,445,953 B1 | 9/2002 | Bulkes et al. |
| 6,453,200 B1 | 9/2002 | Koslar |
| 6,459,929 B1 | 10/2002 | Hopper et al. |
| 6,470,215 B1 | 10/2002 | Kraus et al. |
| 6,471,645 B1 | 10/2002 | Warkentin et al. |
| 6,480,745 B2 | 11/2002 | Nelson et al. |
| 6,487,443 B2 | 11/2002 | Olson et al. |
| 6,490,487 B1 | 12/2002 | Kraus et al. |
| 6,498,951 B1 | 12/2002 | Larson et al. |
| 6,507,755 B1 | 1/2003 | Gozani et al. |
| 6,507,759 B1 | 1/2003 | Prutchi et al. |
| 6,512,940 B1 | 1/2003 | Brabec et al. |
| 6,522,915 B1 | 2/2003 | Ceballos et al. |
| 6,526,311 B2 | 2/2003 | Begemann |
| 6,539,253 B2 | 3/2003 | Thompson et al. |
| 6,542,775 B2 | 4/2003 | Ding et al. |
| 6,553,258 B2 | 4/2003 | Stahmann et al. |
| 6,561,975 B1 | 5/2003 | Pool et al. |
| 6,564,807 B1 | 5/2003 | Schulman et al. |
| 6,574,506 B2 | 6/2003 | Kramer et al. |
| 6,584,351 B1 | 6/2003 | Ekwall |
| 6,584,352 B2 | 6/2003 | Combs et al. |
| 6,597,948 B1 | 7/2003 | Rockwell et al. |
| 6,597,951 B2 | 7/2003 | Kramer et al. |
| 6,622,046 B2 | 9/2003 | Fraley et al. |
| 6,628,985 B2 | 9/2003 | Sweeney et al. |
| 6,647,292 B1 | 11/2003 | Bardy et al. |
| 6,666,844 B1 | 12/2003 | Igo et al. |
| 6,689,117 B2 | 2/2004 | Sweeney et al. |
| 6,690,959 B2 | 2/2004 | Thompson |
| 6,694,189 B2 | 2/2004 | Begemann |
| 6,704,602 B2 | 3/2004 | Berg et al. |
| 6,718,212 B2 | 4/2004 | Parry et al. |
| 6,721,597 B1 | 4/2004 | Bardy et al. |
| 6,738,670 B1 | 5/2004 | Almendinger et al. |
| 6,746,797 B2 | 6/2004 | Benson et al. |
| 6,749,566 B2 | 6/2004 | Russ |
| 6,758,810 B2 | 7/2004 | Lebel et al. |
| 6,763,269 B2 | 7/2004 | Cox |
| 6,778,860 B2 | 8/2004 | Ostroff et al. |
| 6,788,971 B1 | 9/2004 | Sloman et al. |
| 6,788,974 B2 | 9/2004 | Bardy et al. |
| 6,804,558 B2 | 10/2004 | Haller et al. |
| 6,807,442 B1 | 10/2004 | Myklebust et al. |
| 6,847,844 B2 | 1/2005 | Sun et al. |
| 6,871,095 B2 | 3/2005 | Stahmann et al. |
| 6,878,112 B2 | 4/2005 | Linberg et al. |
| 6,885,889 B2 | 4/2005 | Chinchoy |
| 6,892,094 B2 | 5/2005 | Ousdigian et al. |
| 6,897,788 B2 | 5/2005 | Khair et al. |
| 6,904,315 B2 | 6/2005 | Panken et al. |
| 6,922,592 B2 | 7/2005 | Thompson et al. |
| 6,931,282 B2 | 8/2005 | Esler |
| 6,934,585 B1 | 8/2005 | Schloss et al. |
| 6,957,107 B2 | 10/2005 | Rogers et al. |
| 6,978,176 B2 | 12/2005 | Lattouf |
| 6,985,773 B2 | 1/2006 | Von Arx et al. |
| 6,990,375 B2 | 1/2006 | Kloss et al. |
| 7,001,366 B2 | 2/2006 | Ballard |
| 7,003,350 B2 | 2/2006 | Denker et al. |
| 7,006,864 B2 | 2/2006 | Echt et al. |
| 7,013,178 B2 | 3/2006 | Reinke et al. |
| 7,027,871 B2 | 4/2006 | Burnes et al. |
| 7,050,849 B2 | 5/2006 | Echt et al. |
| 7,060,031 B2 | 6/2006 | Webb et al. |
| 7,063,693 B2 | 6/2006 | Guenst |
| 7,082,336 B2 | 7/2006 | Ransbury et al. |
| 7,085,606 B2 | 8/2006 | Flach et al. |
| 7,092,758 B2 | 8/2006 | Sun et al. |
| 7,110,824 B2 | 9/2006 | Amundson et al. |
| 7,120,504 B2 | 10/2006 | Osypka |
| 7,130,681 B2 | 10/2006 | Gebhardt et al. |
| 7,139,613 B2 | 11/2006 | Reinke et al. |
| 7,142,912 B2 | 11/2006 | Wagner et al. |
| 7,146,225 B2 | 12/2006 | Guenst et al. |

(56) References Cited

U.S. PATENT DOCUMENTS

| | | |
|---|---|---|
| 7,146,226 B2 | 12/2006 | Lau et al. |
| 7,149,581 B2 | 12/2006 | Goedeke |
| 7,149,588 B2 | 12/2006 | Lau et al. |
| 7,158,839 B2 | 1/2007 | Lau |
| 7,162,307 B2 | 1/2007 | Patrias |
| 7,164,952 B2 | 1/2007 | Lau et al. |
| 7,177,700 B1 | 2/2007 | Cox |
| 7,181,505 B2 | 2/2007 | Haller et al. |
| 7,184,830 B2 | 2/2007 | Echt et al. |
| 7,186,214 B2 | 3/2007 | Ness |
| 7,191,015 B2 | 3/2007 | Lamson et al. |
| 7,200,437 B1 | 4/2007 | Nabutovsky et al. |
| 7,200,439 B2 | 4/2007 | Zdeblick et al. |
| 7,206,423 B1 | 4/2007 | Feng et al. |
| 7,209,785 B2 | 4/2007 | Kim et al. |
| 7,209,790 B2 | 4/2007 | Thompson et al. |
| 7,211,884 B1 | 5/2007 | Davis et al. |
| 7,212,871 B1 | 5/2007 | Morgan |
| 7,226,440 B2 | 6/2007 | Gelfand et al. |
| 7,228,183 B2 | 6/2007 | Sun et al. |
| 7,236,821 B2 | 6/2007 | Cates et al. |
| 7,236,829 B1 | 6/2007 | Farazi et al. |
| 7,254,448 B2 | 8/2007 | Almendinger et al. |
| 7,260,436 B2 | 8/2007 | Kilgore et al. |
| 7,270,669 B1 | 9/2007 | Sra |
| 7,272,448 B1 | 9/2007 | Morgan et al. |
| 7,277,755 B1 | 10/2007 | Falkenberg et al. |
| 7,280,872 B1 | 10/2007 | Mosesov et al. |
| 7,288,096 B2 | 10/2007 | Chin |
| 7,289,847 B1 | 10/2007 | Gill et al. |
| 7,289,852 B2 | 10/2007 | Helfinstine et al. |
| 7,289,853 B1 | 10/2007 | Campbell et al. |
| 7,289,855 B2 | 10/2007 | Nghiem et al. |
| 7,302,294 B2 | 11/2007 | Kamath et al. |
| 7,305,266 B1 | 12/2007 | Kroll |
| 7,310,556 B2 | 12/2007 | Bulkes |
| 7,319,905 B1 | 1/2008 | Morgan et al. |
| 7,321,798 B2 | 1/2008 | Muhlenberg et al. |
| 7,333,853 B2 | 2/2008 | Mazar et al. |
| 7,336,994 B2 | 2/2008 | Hettrick et al. |
| 7,347,819 B2 | 3/2008 | Lebel et al. |
| 7,366,572 B2 | 4/2008 | Heruth et al. |
| 7,373,207 B2 | 5/2008 | Lattouf |
| 7,384,403 B2 | 6/2008 | Sherman |
| 7,386,342 B1 | 6/2008 | Falkenberg et al. |
| 7,392,090 B2 | 6/2008 | Sweeney et al. |
| 7,406,105 B2 | 7/2008 | DelMain et al. |
| 7,406,349 B2 | 7/2008 | Seeberger et al. |
| 7,410,497 B2 | 8/2008 | Hastings et al. |
| 7,425,200 B2 | 9/2008 | Brockway et al. |
| 7,428,438 B2 | 9/2008 | Parramon et al. |
| 7,433,739 B1 | 10/2008 | Salys et al. |
| 7,496,409 B2 | 2/2009 | Greenhut et al. |
| 7,496,410 B2 | 2/2009 | Heil |
| 7,502,652 B2 | 3/2009 | Gaunt et al. |
| 7,512,448 B2 | 3/2009 | Malick et al. |
| 7,515,969 B2 | 4/2009 | Tockman et al. |
| 7,526,342 B2 | 4/2009 | Chin et al. |
| 7,529,589 B2 | 5/2009 | Williams et al. |
| 7,532,933 B2 | 5/2009 | Hastings et al. |
| 7,536,222 B2 | 5/2009 | Bardy et al. |
| 7,536,224 B2 | 5/2009 | Ritscher et al. |
| 7,539,541 B2 | 5/2009 | Quiles et al. |
| 7,544,197 B2 | 6/2009 | Kelsch et al. |
| 7,558,631 B2 | 7/2009 | Cowan et al. |
| 7,565,195 B1 | 7/2009 | Kroll et al. |
| 7,584,002 B2 | 9/2009 | Burnes et al. |
| 7,590,455 B2 | 9/2009 | Heruth et al. |
| 7,606,621 B2 | 10/2009 | Brisken et al. |
| 7,610,088 B2 | 10/2009 | Chinchoy |
| 7,610,092 B2 | 10/2009 | Cowan et al. |
| 7,610,099 B2 | 10/2009 | Almendinger et al. |
| 7,610,104 B2 | 10/2009 | Kaplan et al. |
| 7,616,991 B2 | 11/2009 | Mann et al. |
| 7,617,001 B2 | 11/2009 | Penner et al. |
| 7,617,007 B2 | 11/2009 | Williams et al. |
| 7,630,767 B1 | 12/2009 | Poore et al. |
| 7,634,313 B1 | 12/2009 | Kroll et al. |
| 7,637,867 B2 | 12/2009 | Zdeblick |
| 7,640,060 B2 | 12/2009 | Zdeblick |
| 7,647,109 B2 | 1/2010 | Hastings et al. |
| 7,650,186 B2 | 1/2010 | Hastings et al. |
| 7,657,311 B2 | 2/2010 | Bardy et al. |
| 7,668,596 B2 | 2/2010 | Von Arx et al. |
| 7,682,316 B2 | 3/2010 | Anderson et al. |
| 7,691,047 B2 | 4/2010 | Ferrari |
| 7,702,392 B2 | 4/2010 | Echt et al. |
| 7,713,194 B2 | 5/2010 | Zdeblick |
| 7,713,195 B2 | 5/2010 | Zdeblick |
| 7,729,783 B2 | 6/2010 | Michels et al. |
| 7,734,333 B2 | 6/2010 | Ghanem et al. |
| 7,734,343 B2 | 6/2010 | Ransbury et al. |
| 7,738,958 B2 | 6/2010 | Zdeblick et al. |
| 7,738,964 B2 | 6/2010 | Von Arx et al. |
| 7,742,812 B2 | 6/2010 | Ghanem et al. |
| 7,742,816 B2 | 6/2010 | Masoud et al. |
| 7,742,822 B2 | 6/2010 | Masoud et al. |
| 7,743,151 B2 | 6/2010 | Vallapureddy et al. |
| 7,747,335 B2 | 6/2010 | Williams |
| 7,751,881 B2 | 7/2010 | Cowan et al. |
| 7,758,521 B2 | 7/2010 | Morris et al. |
| 7,761,150 B2 | 7/2010 | Ghanem et al. |
| 7,761,164 B2 | 7/2010 | Verhoef et al. |
| 7,765,001 B2 | 7/2010 | Echt et al. |
| 7,769,452 B2 | 8/2010 | Ghanem et al. |
| 7,783,362 B2 | 8/2010 | Whitehurst et al. |
| 7,792,588 B2 | 9/2010 | Harding |
| 7,797,059 B1 | 9/2010 | Bornzin et al. |
| 7,801,596 B2 | 9/2010 | Fischell et al. |
| 7,809,438 B2 | 10/2010 | Echt et al. |
| 7,840,281 B2 | 11/2010 | Kveen et al. |
| 7,844,331 B2 | 11/2010 | Li et al. |
| 7,844,348 B2 | 11/2010 | Swoyer et al. |
| 7,846,088 B2 | 12/2010 | Ness |
| 7,848,815 B2 | 12/2010 | Brisken et al. |
| 7,848,823 B2 | 12/2010 | Drasler et al. |
| 7,860,455 B2 | 12/2010 | Fukumoto et al. |
| 7,871,433 B2 | 1/2011 | Lattouf |
| 7,877,136 B1 | 1/2011 | Moffitt et al. |
| 7,877,142 B2 | 1/2011 | Moaddeb et al. |
| 7,881,786 B2 | 2/2011 | Jackson |
| 7,881,798 B2 | 2/2011 | Miesel et al. |
| 7,881,810 B1 | 2/2011 | Chitre et al. |
| 7,890,173 B2 | 2/2011 | Brisken et al. |
| 7,890,181 B2 | 2/2011 | Denzene et al. |
| 7,890,192 B1 | 2/2011 | Kelsch et al. |
| 7,894,885 B2 | 2/2011 | Bartal et al. |
| 7,894,894 B2 | 2/2011 | Stadler et al. |
| 7,894,907 B2 | 2/2011 | Cowan et al. |
| 7,894,910 B2 | 2/2011 | Cowan et al. |
| 7,894,915 B1 | 2/2011 | Chitre et al. |
| 7,899,537 B1 | 3/2011 | Kroll et al. |
| 7,899,541 B2 | 3/2011 | Cowan et al. |
| 7,899,542 B2 | 3/2011 | Cowan et al. |
| 7,899,554 B2 | 3/2011 | Williams et al. |
| 7,901,360 B1 | 3/2011 | Yang et al. |
| 7,904,170 B2 | 3/2011 | Harding |
| 7,907,993 B2 | 3/2011 | Ghanem et al. |
| 7,920,928 B1 | 4/2011 | Yang et al. |
| 7,925,343 B1 | 4/2011 | Min et al. |
| 7,930,022 B2 | 4/2011 | Zhang et al. |
| 7,930,040 B1 | 4/2011 | Kelsch et al. |
| 7,937,135 B2 | 5/2011 | Ghanem et al. |
| 7,937,148 B2 | 5/2011 | Jacobson |
| 7,937,161 B2 | 5/2011 | Hastings et al. |
| 7,941,214 B2 | 5/2011 | Kleckner et al. |
| 7,945,333 B2 | 5/2011 | Jacobson |
| 7,946,997 B2 | 5/2011 | Hübinette |
| 7,949,404 B2 | 5/2011 | Hill |
| 7,949,405 B2 | 5/2011 | Feher |
| 7,953,486 B2 | 5/2011 | Daum et al. |
| 7,953,493 B2 | 5/2011 | Fowler et al. |
| 7,962,202 B2 | 6/2011 | Bhunia |
| 7,974,702 B1 | 7/2011 | Fain et al. |

(56) References Cited

U.S. PATENT DOCUMENTS

| | | |
|---|---|---|
| 7,979,136 B2 | 7/2011 | Young et al. |
| 7,983,753 B2 | 7/2011 | Severin |
| 7,991,467 B2 | 8/2011 | Markowitz et al. |
| 7,991,471 B2 | 8/2011 | Ghanem et al. |
| 7,996,087 B2 | 8/2011 | Cowan et al. |
| 8,000,791 B2 | 8/2011 | Sunagawa et al. |
| 8,000,807 B2 | 8/2011 | Morris et al. |
| 8,001,975 B2 | 8/2011 | DiSilvestro et al. |
| 8,002,700 B2 | 8/2011 | Ferek-Petric et al. |
| 8,010,209 B2 | 8/2011 | Jacobson |
| 8,019,419 B1 | 9/2011 | Panescu et al. |
| 8,019,434 B2 | 9/2011 | Quiles et al. |
| 8,027,727 B2 | 9/2011 | Freeberg |
| 8,027,729 B2 | 9/2011 | Sunagawa et al. |
| 8,032,219 B2 | 10/2011 | Neumann et al. |
| 8,036,743 B2 | 10/2011 | Savage et al. |
| 8,046,079 B2 | 10/2011 | Bange et al. |
| 8,046,080 B2 | 10/2011 | Von Arx et al. |
| 8,050,297 B2 | 11/2011 | DelMain et al. |
| 8,050,759 B2 | 11/2011 | Stegemann et al. |
| 8,050,774 B2 | 11/2011 | Kveen et al. |
| 8,055,345 B2 | 11/2011 | Li et al. |
| 8,055,350 B2 | 11/2011 | Roberts |
| 8,060,212 B1 | 11/2011 | Rios et al. |
| 8,065,018 B2 | 11/2011 | Haubrich et al. |
| 8,073,542 B2 | 12/2011 | Doerr |
| 8,078,278 B2 | 12/2011 | Penner |
| 8,078,283 B2 | 12/2011 | Cowan et al. |
| 8,095,123 B2 | 1/2012 | Gray |
| 8,102,789 B2 | 1/2012 | Rosar et al. |
| 8,103,359 B2 | 1/2012 | Reddy |
| 8,103,361 B2 | 1/2012 | Moser |
| 8,112,148 B2 | 2/2012 | Giftakis et al. |
| 8,114,021 B2 | 2/2012 | Robertson et al. |
| 8,121,680 B2 | 2/2012 | Falkenberg et al. |
| 8,123,684 B2 | 2/2012 | Zdeblick |
| 8,126,545 B2 | 2/2012 | Flach et al. |
| 8,131,334 B2 | 3/2012 | Lu et al. |
| 8,140,161 B2 | 3/2012 | Willerton et al. |
| 8,150,521 B2 | 4/2012 | Crowley et al. |
| 8,160,672 B2 | 4/2012 | Kim et al. |
| 8,160,702 B2 | 4/2012 | Mann et al. |
| 8,160,704 B2 | 4/2012 | Freeberg |
| 8,165,694 B2 | 4/2012 | Carbanaru et al. |
| 8,175,715 B1 | 5/2012 | Cox |
| 8,180,451 B2 | 5/2012 | Hickman et al. |
| 8,185,213 B2 | 5/2012 | Kveen et al. |
| 8,187,161 B2 | 5/2012 | Li et al. |
| 8,195,293 B2 | 6/2012 | Limousin et al. |
| 8,204,595 B2 | 6/2012 | Pianca et al. |
| 8,204,605 B2 | 6/2012 | Hastings et al. |
| 8,209,014 B2 | 6/2012 | Doerr |
| 8,214,043 B2 | 7/2012 | Matos |
| 8,224,244 B2 | 7/2012 | Kim et al. |
| 8,229,556 B2 | 7/2012 | Li |
| 8,233,985 B2 | 7/2012 | Bulkes et al. |
| 8,262,578 B1 | 9/2012 | Bharmi et al. |
| 8,265,748 B2 | 9/2012 | Liu et al. |
| 8,265,757 B2 | 9/2012 | Mass et al. |
| 8,280,521 B2 | 10/2012 | Haubrich et al. |
| 8,285,387 B2 | 10/2012 | Utsi et al. |
| 8,290,598 B2 | 10/2012 | Boon et al. |
| 8,290,600 B2 | 10/2012 | Hastings et al. |
| 8,295,939 B2 | 10/2012 | Jacobson |
| 8,301,254 B2 | 10/2012 | Mosesov et al. |
| 8,315,701 B2 | 11/2012 | Cowan et al. |
| 8,315,708 B2 | 11/2012 | Berthelsdorf et al. |
| 8,321,021 B2 | 11/2012 | Kisker et al. |
| 8,321,036 B2 | 11/2012 | Brockway et al. |
| 8,332,036 B2 | 12/2012 | Hastings et al. |
| 8,335,563 B2 | 12/2012 | Stessman |
| 8,335,568 B2 | 12/2012 | Heruth et al. |
| 8,340,750 B2 | 12/2012 | Prakash et al. |
| 8,340,780 B2 | 12/2012 | Hastings et al. |
| 8,352,025 B2 | 1/2013 | Jacobson |
| 8,352,028 B2 | 1/2013 | Wenger |
| 8,352,038 B2 | 1/2013 | Mao et al. |
| 8,359,098 B2 | 1/2013 | Lund et al. |
| 8,364,261 B2 | 1/2013 | Stubbs et al. |
| 8,364,276 B2 | 1/2013 | Willis |
| 8,369,959 B2 | 2/2013 | Meskens |
| 8,369,962 B2 | 2/2013 | Abrahamson |
| 8,380,320 B2 | 2/2013 | Spital |
| 8,386,051 B2 | 2/2013 | Rys |
| 8,391,981 B2 | 3/2013 | Mosesov |
| 8,391,990 B2 | 3/2013 | Smith et al. |
| 8,406,874 B2 | 3/2013 | Liu et al. |
| 8,406,879 B2 | 3/2013 | Shuros et al. |
| 8,406,886 B2 | 3/2013 | Gaunt et al. |
| 8,412,352 B2 | 4/2013 | Griswold et al. |
| 8,417,340 B2 | 4/2013 | Goossen |
| 8,417,341 B2 | 4/2013 | Freeberg |
| 8,423,149 B2 | 4/2013 | Hennig |
| 8,428,722 B2 | 4/2013 | Verhoef et al. |
| 8,433,402 B2 | 4/2013 | Ruben et al. |
| 8,433,409 B2 | 4/2013 | Johnson et al. |
| 8,433,420 B2 | 4/2013 | Bange et al. |
| 8,447,412 B2 | 5/2013 | Dal Molin et al. |
| 8,452,413 B2 | 5/2013 | Young et al. |
| 8,457,740 B2 | 6/2013 | Osche |
| 8,457,742 B2 | 6/2013 | Jacobson |
| 8,457,744 B2 | 6/2013 | Janzig et al. |
| 8,457,761 B2 | 6/2013 | Wariar |
| 8,478,407 B2 | 7/2013 | Demmer et al. |
| 8,478,408 B2 | 7/2013 | Hastings et al. |
| 8,478,431 B2 | 7/2013 | Griswold et al. |
| 8,494,632 B2 | 7/2013 | Sun et al. |
| 8,504,156 B2 | 8/2013 | Bonner et al. |
| 8,509,910 B2 | 8/2013 | Sowder et al. |
| 8,515,559 B2 | 8/2013 | Roberts et al. |
| 8,525,340 B2 | 9/2013 | Eckhardt et al. |
| 8,527,068 B2 | 9/2013 | Ostroff |
| 8,532,790 B2 | 9/2013 | Griswold |
| 8,538,526 B2 | 9/2013 | Stahmann et al. |
| 8,541,131 B2 | 9/2013 | Lund et al. |
| 8,543,205 B2 | 9/2013 | Ostroff |
| 8,547,248 B2 | 10/2013 | Zdeblick et al. |
| 8,548,605 B2 | 10/2013 | Ollivier |
| 8,554,333 B2 | 10/2013 | Wu et al. |
| 8,565,882 B2 | 10/2013 | Matos |
| 8,565,897 B2 | 10/2013 | Regnier et al. |
| 8,571,678 B2 | 10/2013 | Wang |
| 8,577,327 B2 | 11/2013 | Makdissi et al. |
| 8,588,926 B2 | 11/2013 | Moore et al. |
| 8,612,002 B2 | 12/2013 | Faltys et al. |
| 8,615,310 B2 | 12/2013 | Khairkhahan et al. |
| 8,626,280 B2 | 1/2014 | Allavatam et al. |
| 8,626,294 B2 | 1/2014 | Sheldon et al. |
| 8,634,908 B2 | 1/2014 | Cowan |
| 8,634,912 B2 | 1/2014 | Bornzin et al. |
| 8,634,919 B1 | 1/2014 | Hou et al. |
| 8,639,335 B2 | 1/2014 | Peichel et al. |
| 8,644,934 B2 | 2/2014 | Hastings et al. |
| 8,649,859 B2 | 2/2014 | Smith et al. |
| 8,670,842 B1 | 3/2014 | Bornzin et al. |
| 8,676,319 B2 | 3/2014 | Knoll |
| 8,676,335 B2 | 3/2014 | Katoozi et al. |
| 8,700,173 B2 | 4/2014 | Edlund |
| 8,700,181 B2 | 4/2014 | Bornzin et al. |
| 8,705,599 B2 | 4/2014 | dal Molin et al. |
| 8,718,766 B2 | 5/2014 | Wahlberg |
| 8,718,773 B2 | 5/2014 | Willis et al. |
| 8,725,260 B2 | 5/2014 | Shuros et al. |
| 8,738,133 B2 | 5/2014 | Shuros et al. |
| 8,738,147 B2 | 5/2014 | Hastings et al. |
| 8,744,555 B2 | 6/2014 | Allavatam et al. |
| 8,744,572 B1 | 6/2014 | Greenhut et al. |
| 8,747,314 B2 | 6/2014 | Stahmann et al. |
| 8,755,884 B2 | 6/2014 | Demmer et al. |
| 8,758,365 B2 | 6/2014 | Bonner et al. |
| 8,768,483 B2 | 7/2014 | Schmitt et al. |
| 8,774,572 B2 | 7/2014 | Hamamoto |
| 8,781,605 B2 | 7/2014 | Bornzin et al. |
| 8,788,035 B2 | 7/2014 | Jacobson |

(56) References Cited

U.S. PATENT DOCUMENTS

| | | |
|---|---|---|
| 8,788,053 B2 | 7/2014 | Jacobson |
| 8,798,740 B2 | 8/2014 | Samade et al. |
| 8,798,745 B2 | 8/2014 | Jacobson |
| 8,798,762 B2 | 8/2014 | Fain et al. |
| 8,798,770 B2 | 8/2014 | Reddy |
| 8,805,505 B1 | 8/2014 | Roberts |
| 8,805,528 B2 | 8/2014 | Corndorf |
| 8,812,109 B2 | 8/2014 | Blomqvist et al. |
| 8,818,504 B2 | 8/2014 | Bodner et al. |
| 8,827,913 B2 | 9/2014 | Havel et al. |
| 8,831,747 B1 | 9/2014 | Min et al. |
| 8,855,789 B2 | 10/2014 | Jacobson |
| 8,868,186 B2 | 10/2014 | Kroll |
| 8,886,339 B2 | 11/2014 | Faltys et al. |
| 8,903,473 B2 | 12/2014 | Rogers et al. |
| 8,903,500 B2 | 12/2014 | Smith et al. |
| 8,903,513 B2 | 12/2014 | Ollivier |
| 8,909,336 B2 | 12/2014 | Navarro-Paredes et al. |
| 8,914,131 B2 | 12/2014 | Bornzin et al. |
| 8,923,795 B2 | 12/2014 | Makdissi et al. |
| 8,923,963 B2 | 12/2014 | Bonner et al. |
| 8,938,300 B2 | 1/2015 | Rosero |
| 8,942,806 B2 | 1/2015 | Sheldon et al. |
| 8,958,892 B2 | 2/2015 | Khairkhahan et al. |
| 8,977,358 B2 | 3/2015 | Ewert et al. |
| 8,989,873 B2 | 3/2015 | Locsin |
| 8,996,109 B2 | 3/2015 | Karst et al. |
| 9,002,467 B2 | 4/2015 | Smith et al. |
| 9,008,776 B2 | 4/2015 | Cowan et al. |
| 9,008,777 B2 | 4/2015 | Dianaty et al. |
| 9,014,818 B2 | 4/2015 | Deterre et al. |
| 9,017,341 B2 | 4/2015 | Bornzin et al. |
| 9,020,611 B2 | 4/2015 | Khairkhahan et al. |
| 9,037,262 B2 | 5/2015 | Regnier et al. |
| 9,042,984 B2 | 5/2015 | Demmer et al. |
| 9,072,911 B2 | 7/2015 | Hastings et al. |
| 9,072,913 B2 | 7/2015 | Jacobson |
| 9,155,882 B2 | 10/2015 | Grubac et al. |
| 9,168,372 B2 | 10/2015 | Fain |
| 9,168,380 B1 | 10/2015 | Greenhut et al. |
| 9,168,383 B2 | 10/2015 | Jacobson et al. |
| 9,180,285 B2 | 11/2015 | Moore et al. |
| 9,192,774 B2 | 11/2015 | Jacobson |
| 9,205,225 B2 | 12/2015 | Khairkhahan et al. |
| 9,216,285 B1 | 12/2015 | Boling et al. |
| 9,216,293 B2 | 12/2015 | Berthiaume et al. |
| 9,216,298 B2 | 12/2015 | Jacobson |
| 9,227,077 B2 | 1/2016 | Jacobson |
| 9,238,145 B2 | 1/2016 | Wenzel et al. |
| 9,242,102 B2 | 1/2016 | Khairkhahan et al. |
| 9,242,113 B2 | 1/2016 | Smith et al. |
| 9,248,300 B2 | 2/2016 | Rys et al. |
| 9,265,436 B2 | 2/2016 | Min et al. |
| 9,265,962 B2 | 2/2016 | Dianaty et al. |
| 9,272,155 B2 | 3/2016 | Ostroff |
| 9,278,218 B2 | 3/2016 | Karst et al. |
| 9,278,229 B1 | 3/2016 | Reinke et al. |
| 9,283,381 B2 | 3/2016 | Grubac et al. |
| 9,283,382 B2 | 3/2016 | Berthiaume et al. |
| 9,289,612 B1 | 3/2016 | Sambelashvili et al. |
| 9,302,115 B2 | 4/2016 | Molin et al. |
| 9,333,364 B2 | 5/2016 | Echt et al. |
| 9,358,387 B2 | 6/2016 | Suwito et al. |
| 9,358,400 B2 | 6/2016 | Jacobson |
| 9,364,675 B2 | 6/2016 | Deterre et al. |
| 9,370,663 B2 | 6/2016 | Moulder |
| 9,375,580 B2 | 6/2016 | Bonner et al. |
| 9,375,581 B2 | 6/2016 | Baru et al. |
| 9,381,365 B2 | 7/2016 | Kibler et al. |
| 9,393,424 B2 | 7/2016 | Demmer et al. |
| 9,393,436 B2 | 7/2016 | Doerr |
| 9,399,139 B2 | 7/2016 | Demmer et al. |
| 9,399,140 B2 | 7/2016 | Cho et al. |
| 9,409,033 B2 | 8/2016 | Jacobson |
| 9,427,594 B1 * | 8/2016 | Bornzin ............... A61B 5/6852 |
| 9,433,368 B2 | 9/2016 | Stahmann et al. |
| 9,433,780 B2 | 9/2016 | Régnier et al. |
| 9,457,193 B2 | 10/2016 | Klimovitch et al. |
| 9,492,668 B2 | 11/2016 | Sheldon et al. |
| 9,492,669 B2 | 11/2016 | Demmer et al. |
| 9,492,674 B2 | 11/2016 | Schmidt et al. |
| 9,492,677 B2 | 11/2016 | Greenhut et al. |
| 9,511,233 B2 | 12/2016 | Sambelashvili |
| 9,511,236 B2 | 12/2016 | Varady et al. |
| 9,511,237 B2 | 12/2016 | Deterre et al. |
| 9,522,276 B2 | 12/2016 | Shen et al. |
| 9,522,280 B2 | 12/2016 | Fishler et al. |
| 9,526,522 B2 | 12/2016 | Wood et al. |
| 9,526,891 B2 | 12/2016 | Eggen et al. |
| 9,526,909 B2 | 12/2016 | Stahmann et al. |
| 9,533,163 B2 | 1/2017 | Klimovitch et al. |
| 9,561,382 B2 | 2/2017 | Persson et al. |
| 9,566,012 B2 | 2/2017 | Greenhut et al. |
| 9,636,511 B2 | 5/2017 | Carney et al. |
| 9,669,223 B2 | 6/2017 | Auricchio et al. |
| 9,687,654 B2 | 6/2017 | Sheldon et al. |
| 9,687,655 B2 | 6/2017 | Pertijs et al. |
| 9,687,659 B2 | 6/2017 | Von Arx et al. |
| 9,694,186 B2 | 7/2017 | Carney et al. |
| 9,782,594 B2 | 10/2017 | Stahmann et al. |
| 9,782,601 B2 | 10/2017 | Ludwig |
| 9,789,317 B2 | 10/2017 | Greenhut et al. |
| 9,789,319 B2 | 10/2017 | Sambelashvili |
| 9,808,617 B2 | 11/2017 | Ostroff et al. |
| 9,808,628 B2 | 11/2017 | Sheldon et al. |
| 9,808,631 B2 | 11/2017 | Maile et al. |
| 9,808,632 B2 | 11/2017 | Reinke et al. |
| 9,808,633 B2 | 11/2017 | Bonner et al. |
| 9,808,637 B2 | 11/2017 | Sharma et al. |
| 9,855,414 B2 | 1/2018 | Marshall et al. |
| 9,855,430 B2 | 1/2018 | Ghosh et al. |
| 9,855,435 B2 | 1/2018 | Sahabi et al. |
| 9,861,815 B2 | 1/2018 | Tran et al. |
| 10,080,887 B2 | 9/2018 | Schmidt et al. |
| 10,080,888 B2 | 9/2018 | Kelly et al. |
| 10,080,900 B2 | 9/2018 | Ghosh et al. |
| 10,080,903 B2 | 9/2018 | Willis et al. |
| 10,086,206 B2 | 10/2018 | Sambelashvili |
| 10,118,026 B2 | 11/2018 | Grubac et al. |
| 10,124,163 B2 | 11/2018 | Ollivier et al. |
| 10,124,175 B2 | 11/2018 | Berthiaume et al. |
| 10,130,821 B2 | 11/2018 | Grubac et al. |
| 10,137,305 B2 | 11/2018 | Kane et al. |
| 2001/0039374 A1 * | 11/2001 | Schulman ............ A61B 5/14532 600/300 |
| 2002/0032470 A1 | 3/2002 | Linberg |
| 2002/0035376 A1 | 3/2002 | Bardy et al. |
| 2002/0035377 A1 | 3/2002 | Bardy et al. |
| 2002/0035378 A1 | 3/2002 | Bardy et al. |
| 2002/0035380 A1 | 3/2002 | Rissmann et al. |
| 2002/0035381 A1 | 3/2002 | Bardy et al. |
| 2002/0042629 A1 | 4/2002 | Bardy et al. |
| 2002/0042630 A1 | 4/2002 | Bardy et al. |
| 2002/0042634 A1 | 4/2002 | Bardy et al. |
| 2002/0049475 A1 | 4/2002 | Bardy et al. |
| 2002/0052636 A1 | 5/2002 | Bardy et al. |
| 2002/0068958 A1 | 6/2002 | Bardy et al. |
| 2002/0072773 A1 | 6/2002 | Bardy et al. |
| 2002/0082665 A1 | 6/2002 | Haller et al. |
| 2002/0091414 A1 | 7/2002 | Bardy et al. |
| 2002/0095196 A1 | 7/2002 | Linberg |
| 2002/0099423 A1 | 7/2002 | Berg et al. |
| 2002/0103510 A1 | 8/2002 | Bardy et al. |
| 2002/0107545 A1 | 8/2002 | Rissmann et al. |
| 2002/0107546 A1 | 8/2002 | Ostroff et al. |
| 2002/0107547 A1 | 8/2002 | Erlinger et al. |
| 2002/0107548 A1 | 8/2002 | Bardy et al. |
| 2002/0107549 A1 | 8/2002 | Bardy et al. |
| 2002/0107559 A1 | 8/2002 | Sanders et al. |
| 2002/0120299 A1 | 8/2002 | Ostroff et al. |
| 2002/0123674 A1 * | 9/2002 | Plicchi ............... A61B 5/0084 600/300 |
| 2002/0173830 A1 | 11/2002 | Starkweather et al. |
| 2002/0193846 A1 | 12/2002 | Pool et al. |

(56) References Cited

U.S. PATENT DOCUMENTS

| | | |
|---|---|---|
| 2003/0009203 A1 | 1/2003 | Lebel et al. |
| 2003/0028082 A1 | 2/2003 | Thompson |
| 2003/0040779 A1 | 2/2003 | Engmark et al. |
| 2003/0041866 A1 | 3/2003 | Linberg et al. |
| 2003/0045805 A1 | 3/2003 | Sheldon et al. |
| 2003/0088278 A1 | 5/2003 | Bardy et al. |
| 2003/0097153 A1 | 5/2003 | Bardy et al. |
| 2003/0105497 A1 | 6/2003 | Zhu et al. |
| 2003/0105506 A1* | 6/2003 | Krishnan ............... A61N 1/056 607/126 |
| 2003/0114908 A1 | 6/2003 | Flach |
| 2003/0144701 A1 | 7/2003 | Mehra et al. |
| 2003/0187460 A1 | 10/2003 | Chin et al. |
| 2003/0187461 A1 | 10/2003 | Chin |
| 2004/0024435 A1 | 2/2004 | Leckrone et al. |
| 2004/0059392 A1 | 3/2004 | Parramon et al. |
| 2004/0068302 A1 | 4/2004 | Rodgers et al. |
| 2004/0087938 A1 | 5/2004 | Leckrone et al. |
| 2004/0088035 A1 | 5/2004 | Guenst et al. |
| 2004/0102830 A1 | 5/2004 | Williams |
| 2004/0106954 A1 | 6/2004 | Whitehurst et al. |
| 2004/0127959 A1 | 7/2004 | Amundson et al. |
| 2004/0133242 A1 | 7/2004 | Chapman et al. |
| 2004/0147969 A1 | 7/2004 | Mann et al. |
| 2004/0147973 A1 | 7/2004 | Hauser |
| 2004/0167558 A1 | 8/2004 | Igo et al. |
| 2004/0167587 A1 | 8/2004 | Thompson |
| 2004/0172071 A1 | 9/2004 | Bardy et al. |
| 2004/0172077 A1 | 9/2004 | Chinchoy |
| 2004/0172104 A1 | 9/2004 | Berg et al. |
| 2004/0176817 A1 | 9/2004 | Wahlstrand et al. |
| 2004/0176818 A1 | 9/2004 | Wahlstrand et al. |
| 2004/0176830 A1 | 9/2004 | Fang |
| 2004/0186529 A1 | 9/2004 | Bardy et al. |
| 2004/0204673 A1 | 10/2004 | Flaherty |
| 2004/0210292 A1 | 10/2004 | Bardy et al. |
| 2004/0210293 A1 | 10/2004 | Bardy et al. |
| 2004/0210294 A1 | 10/2004 | Bardy et al. |
| 2004/0215308 A1 | 10/2004 | Bardy et al. |
| 2004/0220624 A1 | 11/2004 | Ritscher et al. |
| 2004/0220626 A1 | 11/2004 | Wagner |
| 2004/0220639 A1 | 11/2004 | Mulligan et al. |
| 2004/0230283 A1 | 11/2004 | Prinzen et al. |
| 2004/0249431 A1 | 12/2004 | Ransbury et al. |
| 2004/0260348 A1 | 12/2004 | Bakken et al. |
| 2004/0267303 A1 | 12/2004 | Guenst |
| 2005/0061320 A1 | 3/2005 | Lee et al. |
| 2005/0070962 A1 | 3/2005 | Echt et al. |
| 2005/0102003 A1 | 5/2005 | Grabek et al. |
| 2005/0149138 A1 | 7/2005 | Min et al. |
| 2005/0165466 A1 | 7/2005 | Morris et al. |
| 2005/0182465 A1 | 8/2005 | Ness |
| 2005/0203410 A1 | 9/2005 | Jenkins |
| 2005/0283208 A1 | 12/2005 | Von Arx et al. |
| 2005/0288743 A1 | 12/2005 | Ahn et al. |
| 2006/0042830 A1 | 3/2006 | Maghribi et al. |
| 2006/0052829 A1 | 3/2006 | Sun et al. |
| 2006/0052830 A1 | 3/2006 | Spinelli et al. |
| 2006/0064135 A1 | 3/2006 | Brockway |
| 2006/0064149 A1 | 3/2006 | Belacazar et al. |
| 2006/0085039 A1 | 4/2006 | Hastings et al. |
| 2006/0085041 A1 | 4/2006 | Hastings et al. |
| 2006/0085042 A1 | 4/2006 | Hastings et al. |
| 2006/0095078 A1 | 5/2006 | Tronnes |
| 2006/0106442 A1 | 5/2006 | Richardson et al. |
| 2006/0116746 A1 | 6/2006 | Chin |
| 2006/0135999 A1 | 6/2006 | Bodner et al. |
| 2006/0136004 A1 | 6/2006 | Cowan et al. |
| 2006/0161061 A1 | 7/2006 | Echt et al. |
| 2006/0200002 A1 | 9/2006 | Guenst |
| 2006/0206151 A1 | 9/2006 | Lu |
| 2006/0212079 A1 | 9/2006 | Routh et al. |
| 2006/0241697 A1 | 10/2006 | Libbus et al. |
| 2006/0241701 A1 | 10/2006 | Markowitz et al. |
| 2006/0241705 A1 | 10/2006 | Neumann et al. |
| 2006/0247672 A1 | 11/2006 | Vidlund et al. |
| 2006/0259088 A1 | 11/2006 | Pastore et al. |
| 2006/0265018 A1 | 11/2006 | Smith et al. |
| 2007/0004979 A1 | 1/2007 | Wojciechowicz et al. |
| 2007/0016098 A1 | 1/2007 | Kim et al. |
| 2007/0027508 A1 | 2/2007 | Cowan |
| 2007/0078490 A1 | 4/2007 | Cowan et al. |
| 2007/0088394 A1 | 4/2007 | Jacobson |
| 2007/0088396 A1 | 4/2007 | Jacobson |
| 2007/0088397 A1 | 4/2007 | Jacobson |
| 2007/0088398 A1 | 4/2007 | Jacobson |
| 2007/0088405 A1 | 4/2007 | Jacobson |
| 2007/0135882 A1 | 6/2007 | Drasler et al. |
| 2007/0135883 A1 | 6/2007 | Drasler et al. |
| 2007/0150037 A1 | 6/2007 | Hastings et al. |
| 2007/0150038 A1 | 6/2007 | Hastings et al. |
| 2007/0156190 A1 | 7/2007 | Cinbis |
| 2007/0219525 A1 | 9/2007 | Gelfand et al. |
| 2007/0219590 A1 | 9/2007 | Hastings et al. |
| 2007/0225545 A1 | 9/2007 | Ferrari |
| 2007/0233206 A1 | 10/2007 | Frikart et al. |
| 2007/0239244 A1 | 10/2007 | Morgan et al. |
| 2007/0255376 A1 | 11/2007 | Michels et al. |
| 2007/0276444 A1 | 11/2007 | Gelbart et al. |
| 2007/0293900 A1 | 12/2007 | Sheldon et al. |
| 2007/0293904 A1 | 12/2007 | Gelbart et al. |
| 2008/0004663 A1 | 1/2008 | Jorgenson |
| 2008/0021505 A1 | 1/2008 | Hastings et al. |
| 2008/0021519 A1 | 1/2008 | De Geest et al. |
| 2008/0021532 A1 | 1/2008 | Kveen et al. |
| 2008/0065183 A1 | 3/2008 | Whitehurst et al. |
| 2008/0065185 A1 | 3/2008 | Worley |
| 2008/0071318 A1 | 3/2008 | Brooke et al. |
| 2008/0109054 A1 | 5/2008 | Hastings et al. |
| 2008/0119911 A1 | 5/2008 | Rosero |
| 2008/0130670 A1 | 6/2008 | Kim et al. |
| 2008/0154139 A1 | 6/2008 | Shuros et al. |
| 2008/0154322 A1 | 6/2008 | Jackson et al. |
| 2008/0228234 A1 | 9/2008 | Stancer |
| 2008/0234771 A1 | 9/2008 | Chinchoy et al. |
| 2008/0243217 A1 | 10/2008 | Wildon |
| 2008/0269814 A1 | 10/2008 | Rosero |
| 2008/0269825 A1 | 10/2008 | Chinchoy et al. |
| 2008/0275518 A1 | 11/2008 | Ghanem et al. |
| 2008/0275519 A1 | 11/2008 | Ghanem et al. |
| 2008/0288039 A1 | 11/2008 | Reddy |
| 2008/0294208 A1 | 11/2008 | Willis et al. |
| 2008/0294210 A1 | 11/2008 | Rosero |
| 2008/0294229 A1 | 11/2008 | Friedman et al. |
| 2008/0306359 A1 | 12/2008 | Zdeblick et al. |
| 2009/0018599 A1 | 1/2009 | Hastings et al. |
| 2009/0024180 A1 | 1/2009 | Kisker et al. |
| 2009/0036941 A1 | 2/2009 | Corbucci |
| 2009/0048646 A1 | 2/2009 | Katoozi et al. |
| 2009/0062895 A1 | 3/2009 | Stahmann et al. |
| 2009/0082827 A1 | 3/2009 | Kveen et al. |
| 2009/0082828 A1 | 3/2009 | Ostroff |
| 2009/0088813 A1 | 4/2009 | Brockway et al. |
| 2009/0131907 A1 | 5/2009 | Chin et al. |
| 2009/0135886 A1 | 5/2009 | Robertson et al. |
| 2009/0143835 A1 | 6/2009 | Pastore et al. |
| 2009/0171408 A1 | 7/2009 | Solem |
| 2009/0171414 A1 | 7/2009 | Kelly et al. |
| 2009/0204163 A1 | 8/2009 | Shuros et al. |
| 2009/0204170 A1 | 8/2009 | Hastings et al. |
| 2009/0210024 A1 | 8/2009 | M. |
| 2009/0216292 A1 | 8/2009 | Pless et al. |
| 2009/0234407 A1 | 9/2009 | Hastings et al. |
| 2009/0234411 A1 | 9/2009 | Sambelashvili et al. |
| 2009/0266573 A1 | 10/2009 | Engmark et al. |
| 2009/0275998 A1 | 11/2009 | Burnes et al. |
| 2009/0275999 A1 | 11/2009 | Burnes et al. |
| 2009/0281399 A1 | 11/2009 | Keel et al. |
| 2009/0299447 A1 | 12/2009 | Jensen et al. |
| 2010/0013668 A1 | 1/2010 | Kantervik |
| 2010/0016911 A1 | 1/2010 | Willis et al. |
| 2010/0023085 A1 | 1/2010 | Wu et al. |
| 2010/0030061 A1 | 2/2010 | Canfield et al. |
| 2010/0030327 A1 | 2/2010 | Chatel |

(56) References Cited

U.S. PATENT DOCUMENTS

| | | |
|---|---|---|
| 2010/0042108 A1 | 2/2010 | Hibino |
| 2010/0056871 A1 | 3/2010 | Govari et al. |
| 2010/0063375 A1 | 3/2010 | Kassab et al. |
| 2010/0063562 A1 | 3/2010 | Cowan et al. |
| 2010/0069983 A1 | 3/2010 | Peacock, III et al. |
| 2010/0094367 A1 | 4/2010 | Sen |
| 2010/0114209 A1 | 5/2010 | Krause et al. |
| 2010/0114214 A1 | 5/2010 | Morelli et al. |
| 2010/0125281 A1 | 5/2010 | Jacobson et al. |
| 2010/0168761 A1 | 7/2010 | Kassab et al. |
| 2010/0168819 A1 | 7/2010 | Freeberg |
| 2010/0198288 A1 | 8/2010 | Ostroff |
| 2010/0198304 A1 | 8/2010 | Wang |
| 2010/0217367 A1 | 8/2010 | Belson |
| 2010/0228308 A1 | 9/2010 | Cowan et al. |
| 2010/0234906 A1 | 9/2010 | Koh |
| 2010/0234924 A1 | 9/2010 | Willis |
| 2010/0241185 A1 | 9/2010 | Mahapatra et al. |
| 2010/0249729 A1 | 9/2010 | Morris et al. |
| 2010/0286744 A1 | 11/2010 | Echt et al. |
| 2010/0298841 A1 | 11/2010 | Prinzen et al. |
| 2010/0312309 A1 | 12/2010 | Harding |
| 2011/0022113 A1 | 1/2011 | Zdeblick et al. |
| 2011/0034964 A1* | 2/2011 | Bi .................. A61N 1/025 607/5 |
| 2011/0071586 A1 | 3/2011 | Jacobson |
| 2011/0077708 A1 | 3/2011 | Ostroff |
| 2011/0112600 A1 | 5/2011 | Cowan et al. |
| 2011/0118588 A1 | 5/2011 | Komblau et al. |
| 2011/0118810 A1 | 5/2011 | Cowan et al. |
| 2011/0137187 A1 | 6/2011 | Yang et al. |
| 2011/0144720 A1 | 6/2011 | Cowan et al. |
| 2011/0152970 A1 | 6/2011 | Jollota et al. |
| 2011/0160558 A1 | 6/2011 | Rassatt et al. |
| 2011/0160565 A1 | 6/2011 | Stubbs et al. |
| 2011/0160801 A1 | 6/2011 | Markowitz et al. |
| 2011/0160806 A1 | 6/2011 | Lyden et al. |
| 2011/0166620 A1 | 7/2011 | Cowan et al. |
| 2011/0166621 A1 | 7/2011 | Cowan et al. |
| 2011/0184491 A1 | 7/2011 | Kivi |
| 2011/0190835 A1 | 8/2011 | Brockway et al. |
| 2011/0208260 A1 | 8/2011 | Jacobson |
| 2011/0218587 A1 | 9/2011 | Jacobson |
| 2011/0230734 A1 | 9/2011 | Fain et al. |
| 2011/0237967 A1 | 9/2011 | Moore et al. |
| 2011/0245890 A1 | 10/2011 | Brisben et al. |
| 2011/0251660 A1 | 10/2011 | Griswold |
| 2011/0251662 A1 | 10/2011 | Griswold et al. |
| 2011/0270099 A1 | 11/2011 | Ruben et al. |
| 2011/0270339 A1 | 11/2011 | Murray, III et al. |
| 2011/0270340 A1 | 11/2011 | Pellegrini et al. |
| 2011/0270341 A1 | 11/2011 | Ruben et al. |
| 2011/0276102 A1 | 11/2011 | Cohen |
| 2011/0282423 A1 | 11/2011 | Jacobson |
| 2012/0004527 A1 | 1/2012 | Thompson et al. |
| 2012/0029323 A1 | 2/2012 | Zhao |
| 2012/0041508 A1 | 2/2012 | Rousso et al. |
| 2012/0059433 A1 | 3/2012 | Cowan et al. |
| 2012/0059436 A1 | 3/2012 | Fontaine et al. |
| 2012/0065500 A1 | 3/2012 | Rogers et al. |
| 2012/0078322 A1 | 3/2012 | Dal Molin et al. |
| 2012/0089198 A1 | 4/2012 | Ostroff |
| 2012/0093245 A1 | 4/2012 | Makdissi et al. |
| 2012/0095521 A1 | 4/2012 | Hintz |
| 2012/0095539 A1 | 4/2012 | Khairkhahan et al. |
| 2012/0101540 A1 | 4/2012 | O'Brien et al. |
| 2012/0101553 A1 | 4/2012 | Reddy |
| 2012/0109148 A1 | 5/2012 | Bonner et al. |
| 2012/0109149 A1 | 5/2012 | Bonner et al. |
| 2012/0109236 A1 | 5/2012 | Jacobson et al. |
| 2012/0109259 A1 | 5/2012 | Bond et al. |
| 2012/0116489 A1 | 5/2012 | Khairkhahan et al. |
| 2012/0150251 A1 | 6/2012 | Giftakis et al. |
| 2012/0158111 A1 | 6/2012 | Khairkhahan et al. |
| 2012/0165827 A1 | 6/2012 | Khairkhahan et al. |
| 2012/0172690 A1 | 7/2012 | Anderson et al. |
| 2012/0172891 A1 | 7/2012 | Lee |
| 2012/0172892 A1 | 7/2012 | Grubac et al. |
| 2012/0172942 A1 | 7/2012 | Berg |
| 2012/0197350 A1 | 8/2012 | Roberts et al. |
| 2012/0197373 A1 | 8/2012 | Khairkhahan et al. |
| 2012/0215285 A1 | 8/2012 | Tahmasian et al. |
| 2012/0232565 A1 | 9/2012 | Kveen et al. |
| 2012/0245665 A1 | 9/2012 | Friedman et al. |
| 2012/0277600 A1 | 11/2012 | Greenhut |
| 2012/0277606 A1 | 11/2012 | Ellingson et al. |
| 2012/0283795 A1 | 11/2012 | Stancer et al. |
| 2012/0283807 A1 | 11/2012 | Deterre et al. |
| 2012/0289776 A1 | 11/2012 | Keast et al. |
| 2012/0289815 A1 | 11/2012 | Keast et al. |
| 2012/0290021 A1 | 11/2012 | Saurkar et al. |
| 2012/0290025 A1 | 11/2012 | Keimel |
| 2012/0296381 A1 | 11/2012 | Matos |
| 2012/0303082 A1 | 11/2012 | Dong et al. |
| 2012/0316613 A1 | 12/2012 | Keefe et al. |
| 2013/0012151 A1 | 1/2013 | Hankins |
| 2013/0023975 A1 | 1/2013 | Locsin |
| 2013/0035748 A1 | 2/2013 | Bonner et al. |
| 2013/0041422 A1 | 2/2013 | Jacobson |
| 2013/0053908 A1 | 2/2013 | Smith et al. |
| 2013/0053915 A1 | 2/2013 | Holmstrom et al. |
| 2013/0053921 A1 | 2/2013 | Bonner et al. |
| 2013/0060298 A1 | 3/2013 | Splett et al. |
| 2013/0066169 A1 | 3/2013 | Rys et al. |
| 2013/0072770 A1 | 3/2013 | Rao et al. |
| 2013/0079798 A1 | 3/2013 | Tran et al. |
| 2013/0079861 A1 | 3/2013 | Reinert et al. |
| 2013/0085350 A1 | 4/2013 | Schugt et al. |
| 2013/0085403 A1 | 4/2013 | Gunderson et al. |
| 2013/0085550 A1 | 4/2013 | Polefko et al. |
| 2013/0096649 A1 | 4/2013 | Martin et al. |
| 2013/0103047 A1 | 4/2013 | Steingisser et al. |
| 2013/0103109 A1 | 4/2013 | Jacobson |
| 2013/0110008 A1 | 5/2013 | Bourget et al. |
| 2013/0110127 A1 | 5/2013 | Bornzin et al. |
| 2013/0110192 A1 | 5/2013 | Tran et al. |
| 2013/0110219 A1 | 5/2013 | Bornzin et al. |
| 2013/0116529 A1 | 5/2013 | Min et al. |
| 2013/0116738 A1 | 5/2013 | Samade et al. |
| 2013/0116740 A1 | 5/2013 | Bornzin et al. |
| 2013/0116741 A1 | 5/2013 | Bornzin et al. |
| 2013/0123872 A1 | 5/2013 | Bornzin et al. |
| 2013/0123875 A1 | 5/2013 | Varady et al. |
| 2013/0131591 A1 | 5/2013 | Berthiaume et al. |
| 2013/0131693 A1 | 5/2013 | Berthiaume et al. |
| 2013/0138006 A1 | 5/2013 | Bornzin et al. |
| 2013/0150695 A1 | 6/2013 | Biela et al. |
| 2013/0150911 A1 | 6/2013 | Perschbacher et al. |
| 2013/0150912 A1 | 6/2013 | Perschbacher et al. |
| 2013/0184776 A1 | 7/2013 | Shuros et al. |
| 2013/0192611 A1 | 8/2013 | Taepke, II et al. |
| 2013/0196703 A1 | 8/2013 | Masoud et al. |
| 2013/0197609 A1 | 8/2013 | Moore et al. |
| 2013/0231710 A1 | 9/2013 | Jacobson |
| 2013/0238072 A1 | 9/2013 | Deterre et al. |
| 2013/0238073 A1 | 9/2013 | Makdissi et al. |
| 2013/0253309 A1 | 9/2013 | Allan et al. |
| 2013/0253342 A1 | 9/2013 | Griswold et al. |
| 2013/0253343 A1 | 9/2013 | Waldhauser et al. |
| 2013/0253344 A1 | 9/2013 | Griswold et al. |
| 2013/0253345 A1 | 9/2013 | Griswold et al. |
| 2013/0253346 A1 | 9/2013 | Griswold et al. |
| 2013/0253347 A1 | 9/2013 | Griswold et al. |
| 2013/0261497 A1 | 10/2013 | Pertijs et al. |
| 2013/0265144 A1 | 10/2013 | Banna et al. |
| 2013/0268042 A1 | 10/2013 | Hastings et al. |
| 2013/0274828 A1 | 10/2013 | Willis |
| 2013/0274847 A1 | 10/2013 | Ostroff |
| 2013/0282070 A1 | 10/2013 | Cowan et al. |
| 2013/0282073 A1 | 10/2013 | Cowan et al. |
| 2013/0296727 A1 | 11/2013 | Sullivan et al. |
| 2013/0303872 A1 | 11/2013 | Taff et al. |
| 2013/0324825 A1 | 12/2013 | Ostroff et al. |
| 2013/0325081 A1 | 12/2013 | Karst et al. |

(56) References Cited

U.S. PATENT DOCUMENTS

| | | |
|---|---|---|
| 2013/0345770 A1 | 12/2013 | Dianaty et al. |
| 2014/0012344 A1 | 1/2014 | Hastings et al. |
| 2014/0018876 A1 | 1/2014 | Ostroff |
| 2014/0018877 A1 | 1/2014 | Demmer et al. |
| 2014/0031836 A1 | 1/2014 | Ollivier |
| 2014/0039570 A1 | 2/2014 | Carroll et al. |
| 2014/0039591 A1 | 2/2014 | Drasler et al. |
| 2014/0043146 A1 | 2/2014 | Makdissi et al. |
| 2014/0046395 A1 | 2/2014 | Regnier et al. |
| 2014/0046420 A1 | 2/2014 | Moore et al. |
| 2014/0058240 A1 | 2/2014 | Mothilal et al. |
| 2014/0058494 A1 | 2/2014 | Ostroff et al. |
| 2014/0074114 A1 | 3/2014 | Khairkhahan et al. |
| 2014/0074186 A1 | 3/2014 | Faltys et al. |
| 2014/0094891 A1 | 4/2014 | Pare et al. |
| 2014/0100624 A1 | 4/2014 | Ellingson |
| 2014/0100627 A1 | 4/2014 | Min |
| 2014/0107723 A1 | 4/2014 | Hou et al. |
| 2014/0121719 A1 | 5/2014 | Bonner et al. |
| 2014/0121720 A1 | 5/2014 | Bonner et al. |
| 2014/0121722 A1 | 5/2014 | Sheldon et al. |
| 2014/0128935 A1 | 5/2014 | Kumar et al. |
| 2014/0135865 A1 | 5/2014 | Hastings et al. |
| 2014/0142648 A1 | 5/2014 | Smith et al. |
| 2014/0148675 A1 | 5/2014 | Nordstrom et al. |
| 2014/0148815 A1 | 5/2014 | Wenzel et al. |
| 2014/0155950 A1 | 6/2014 | Hastings et al. |
| 2014/0169162 A1 | 6/2014 | Romano et al. |
| 2014/0172060 A1 | 6/2014 | Bornzin et al. |
| 2014/0180306 A1 | 6/2014 | Grubac et al. |
| 2014/0180366 A1 | 6/2014 | Edlund |
| 2014/0207149 A1 | 7/2014 | Hastings et al. |
| 2014/0207210 A1 | 7/2014 | Willis et al. |
| 2014/0214104 A1* | 7/2014 | Greenhut ............ A61N 1/37288 607/4 |
| 2014/0222015 A1 | 8/2014 | Keast et al. |
| 2014/0222098 A1 | 8/2014 | Baru et al. |
| 2014/0222109 A1 | 8/2014 | Moulder |
| 2014/0228913 A1 | 8/2014 | Molin et al. |
| 2014/0236172 A1 | 8/2014 | Hastings et al. |
| 2014/0243848 A1 | 8/2014 | Auricchio et al. |
| 2014/0255298 A1 | 9/2014 | Cole et al. |
| 2014/0257324 A1 | 9/2014 | Fain |
| 2014/0257422 A1 | 9/2014 | Herken |
| 2014/0257444 A1 | 9/2014 | Cole et al. |
| 2014/0276929 A1 | 9/2014 | Foster et al. |
| 2014/0303704 A1 | 10/2014 | Suwito et al. |
| 2014/0309706 A1 | 10/2014 | Jacobson |
| 2014/0330326 A1 | 11/2014 | Thompson-nauman et al. |
| 2014/0343348 A1 | 11/2014 | Kaplan et al. |
| 2014/0371818 A1 | 12/2014 | Bond et al. |
| 2014/0379041 A1 | 12/2014 | Foster |
| 2015/0025612 A1 | 1/2015 | Haasl et al. |
| 2015/0039041 A1 | 2/2015 | Smith et al. |
| 2015/0045868 A1 | 2/2015 | Bonner et al. |
| 2015/0051609 A1 | 2/2015 | Schmidt et al. |
| 2015/0051610 A1 | 2/2015 | Schmidt et al. |
| 2015/0051611 A1 | 2/2015 | Schmidt et al. |
| 2015/0051612 A1 | 2/2015 | Schmidt et al. |
| 2015/0051613 A1 | 2/2015 | Schmidt et al. |
| 2015/0051614 A1 | 2/2015 | Schmidt et al. |
| 2015/0051615 A1 | 2/2015 | Schmidt et al. |
| 2015/0051616 A1 | 2/2015 | Haasl et al. |
| 2015/0051682 A1 | 2/2015 | Schmidt et al. |
| 2015/0057520 A1 | 2/2015 | Foster et al. |
| 2015/0057558 A1 | 2/2015 | Stahmann et al. |
| 2015/0057721 A1 | 2/2015 | Stahmann et al. |
| 2015/0088155 A1 | 3/2015 | Stahmann et al. |
| 2015/0105836 A1 | 4/2015 | Bonner et al. |
| 2015/0126854 A1 | 5/2015 | Keast et al. |
| 2015/0157861 A1 | 6/2015 | Aghassian |
| 2015/0157866 A1 | 6/2015 | Demmer et al. |
| 2015/0173655 A1 | 6/2015 | Demmer et al. |
| 2015/0190638 A1 | 7/2015 | Smith et al. |
| 2015/0196756 A1 | 7/2015 | Stahmann et al. |
| 2015/0196757 A1 | 7/2015 | Stahmann et al. |
| 2015/0196758 A1 | 7/2015 | Stahmann et al. |
| 2015/0196769 A1* | 7/2015 | Stahmann ............ A61B 5/0028 607/32 |
| 2015/0217119 A1 | 8/2015 | Nikolski et al. |
| 2015/0221898 A1 | 8/2015 | Chi et al. |
| 2015/0224315 A1 | 8/2015 | Stahmann |
| 2015/0224320 A1 | 8/2015 | Stahmann |
| 2015/0230699 A1 | 8/2015 | Berul et al. |
| 2015/0238769 A1 | 8/2015 | Demmer et al. |
| 2015/0258345 A1 | 9/2015 | Smith et al. |
| 2015/0290468 A1 | 10/2015 | Zhang |
| 2015/0297905 A1 | 10/2015 | Greenhut et al. |
| 2015/0297907 A1 | 10/2015 | Zhang |
| 2015/0305637 A1 | 10/2015 | Greenhut et al. |
| 2015/0305638 A1 | 10/2015 | Zhang |
| 2015/0305639 A1 | 10/2015 | Greenhut et al. |
| 2015/0305640 A1 | 10/2015 | Reinke et al. |
| 2015/0305641 A1 | 10/2015 | Stadler et al. |
| 2015/0305642 A1 | 10/2015 | Reinke et al. |
| 2015/0306374 A1 | 10/2015 | Seifert et al. |
| 2015/0306375 A1 | 10/2015 | Marshall et al. |
| 2015/0306401 A1 | 10/2015 | Demmer et al. |
| 2015/0306406 A1 | 10/2015 | Crutchfield et al. |
| 2015/0306407 A1 | 10/2015 | Crutchfield et al. |
| 2015/0306408 A1 | 10/2015 | Greenhut et al. |
| 2015/0321016 A1 | 11/2015 | O'Brien et al. |
| 2015/0328459 A1 | 11/2015 | Chin et al. |
| 2015/0335884 A1 | 11/2015 | Khairkhahan et al. |
| 2016/0015322 A1 | 1/2016 | Anderson et al. |
| 2016/0023000 A1 | 1/2016 | Cho et al. |
| 2016/0030757 A1 | 2/2016 | Jacobson |
| 2016/0033177 A1 | 2/2016 | Barot et al. |
| 2016/0059022 A1 | 3/2016 | Stahmann et al. |
| 2016/0121127 A1 | 5/2016 | Klimovitch et al. |
| 2016/0121128 A1 | 5/2016 | Fishler et al. |
| 2016/0121129 A1 | 5/2016 | Persson et al. |
| 2016/0129263 A1 | 5/2016 | Demmer et al. |
| 2016/0144190 A1 | 5/2016 | Cao et al. |
| 2016/0213919 A1 | 7/2016 | Suwito et al. |
| 2016/0213937 A1 | 7/2016 | Reinke et al. |
| 2016/0213939 A1 | 7/2016 | Carney et al. |
| 2016/0228026 A1 | 8/2016 | Jackson |
| 2016/0317825 A1 | 11/2016 | Jacobson |
| 2016/0367823 A1 | 12/2016 | Cowan et al. |
| 2017/0014629 A1 | 1/2017 | Ghosh et al. |
| 2017/0035315 A1 | 2/2017 | Jackson |
| 2017/0043173 A1 | 2/2017 | Sharma et al. |
| 2017/0043174 A1 | 2/2017 | Greenhut et al. |
| 2017/0056668 A1 | 3/2017 | Maile et al. |
| 2017/0189681 A1 | 7/2017 | Anderson |
| 2017/0281261 A1 | 10/2017 | Shuros et al. |
| 2017/0281952 A1 | 10/2017 | Shuros et al. |
| 2017/0281953 A1 | 10/2017 | Min et al. |
| 2017/0281955 A1 | 10/2017 | Maile et al. |
| 2017/0312531 A1 | 11/2017 | Sawchuk |
| 2018/0256902 A1 | 9/2018 | Toy et al. |
| 2018/0256909 A1 | 9/2018 | Smith et al. |
| 2018/0264262 A1 | 9/2018 | Haasl et al. |
| 2018/0264270 A1 | 9/2018 | Koop et al. |
| 2018/0264272 A1 | 9/2018 | Haasl et al. |
| 2018/0264273 A1 | 9/2018 | Haasl et al. |
| 2018/0264274 A1 | 9/2018 | Haasl et al. |
| 2018/0339160 A1 | 11/2018 | Carroll |

FOREIGN PATENT DOCUMENTS

| | | | |
|---|---|---|---|
| AU | 2014203793 | A1 | 7/2014 |
| CA | 1003904 | A1 | 1/1977 |
| CN | 202933393 | U | 5/2013 |
| EP | 0362611 | A1 | 4/1990 |
| EP | 503823 | A2 | 9/1992 |
| EP | 1702648 | A2 | 9/2006 |
| EP | 1904166 | B1 | 6/2011 |
| EP | 2471452 | A1 | 7/2012 |
| EP | 2433675 | B1 | 1/2013 |
| EP | 2441491 | B1 | 1/2013 |
| EP | 2452721 | B1 | 11/2013 |
| EP | 2662113 | A3 | 11/2013 |

(56) References Cited

FOREIGN PATENT DOCUMENTS

| | | | |
|---|---|---|---|
| EP | 1948296 B1 | 1/2014 | |
| EP | 2188009 B1 * | 11/2015 | ......... A61N 1/36514 |
| EP | 2760541 B1 | 5/2016 | |
| EP | 2833966 B1 | 5/2016 | |
| JP | 2000051373 A | 2/2000 | |
| JP | 2002502640 A | 1/2002 | |
| JP | 2004512105 A | 4/2004 | |
| JP | 2005508208 A | 3/2005 | |
| JP | 2005245215 A | 9/2005 | |
| JP | 2008540040 A | 11/2008 | |
| JP | 5199867 B2 | 2/2013 | |
| WO | 9500202 A1 | 1/1995 | |
| WO | 9636134 A1 | 11/1996 | |
| WO | 9724981 A2 | 7/1997 | |
| WO | 9826840 A1 | 6/1998 | |
| WO | 9939767 A1 | 8/1999 | |
| WO | 0234330 A2 | 5/2002 | |
| WO | 02098282 A2 | 12/2002 | |
| WO | 2005000206 A3 | 1/2005 | |
| WO | 2005042089 A1 | 5/2005 | |
| WO | 2006065394 A1 | 6/2006 | |
| WO | 2006086435 A3 | 8/2006 | |
| WO | 2006113659 A1 | 10/2006 | |
| WO | 2006124833 A3 | 11/2006 | |
| WO | 2007073435 A1 | 6/2007 | |
| WO | 2007075974 A2 | 7/2007 | |
| WO | 2009006531 A1 | 1/2009 | |
| WO | 2012054102 A1 | 4/2012 | |
| WO | 2013080038 A2 | 6/2013 | |
| WO | 2013098644 A3 | 7/2013 | |
| WO | 2013184787 A1 | 12/2013 | |
| WO | 2014120769 A1 | 8/2014 | |
| WO | 2016172109 A1 | 10/2016 | |

OTHER PUBLICATIONS

International Search Report and Written Opinion for Application No. PCT/US2017/052522, 28 pages, dated Dec. 22, 2017.

"Instructions for Use System 1, Leadless Cardiac Pacemaker (LCP) and Delivery Catheter," Nanostim Leadless Pacemakers, pp. 1-28, 2013.

Hachisuka et al., "Development and Performance Analysis of an Intra-Body Communication Device," The 12th International Conference on Solid State Sensors, Actuators and Microsystems, vol. 4A1.3, pp. 1722-1725, 2003.

Seyedi et al., "A Survey on Intrabody Communications for Body Area Network Application," IEEE Transactions on Biomedical Engineering, vol. 60(8): 2067-2079, 2013.

Spickler et al., "Totally Self-Contained Intracardiac Pacemaker," Journal of Electrocardiology, vol. 3(3&4): 324-331, 1970.

Wegmüller, "Intra-Body Communication for Biomedical Sensor Networks," Diss. ETH, No. 17323, 1-173, 2007.

* cited by examiner

IMPLANTABLE CARDIAC MONITOR

CROSS REFERENCE TO RELATED APPLICATIONS

This application claims the benefit of U.S. Provisional Patent Application Ser. No. 62/397,894 filed on Sep. 21, 2016, the disclosure of which is incorporated herein by reference.

TECHNICAL FIELD

The present disclosure generally relates to medical devices, and more particularly, to implantable medical devices for monitoring a patient's heart

BACKGROUND

Implantable medical devices are commonly used today to monitor and/or delivery therapy to a patient, including cardiac simulation therapy. Many patients suffer from heart conditions that can result in a reduced ability of the heart to deliver sufficient amounts of blood to the patient's body. Such heart conditions may lead to slow, rapid, irregular, and/or inefficient heart contractions. To help alleviate some of these conditions, various medical devices (e.g., pacemakers, defibrillators, etc.) are often implanted in a patient's body. Such devices may monitor and in some cases provide electrical stimulation (e.g. pacing, defibrillation, etc.) to the heart to help the heart operate in a more normal, efficient and/or safe manner. Some devices, such as implantable cardiac monitors, can be used separately or in combination with implantable stimulation devices to provide additional sensing and monitoring capability.

SUMMARY

This disclosure generally relates to implantable medical devices, and more particularly, an implantable cardiac monitor (ICM) that can be used alone or in combination with one or more implantable stimulation devices to provide a sensing and/or monitoring capability. In some cases, the ICM may provide additional sensing and/or monitoring for a leadless cardiac pacemaker (LCP) implanted in a patient's heart and/or a subcutaneous implantable cardioverter defibrillator (SICD) implanted subcutaneously in a patient. In some cases, an ICM may be configured to be deployed intravascularly at a position where the ICM may provide additional sensing and/or monitoring capability.

In one example of the disclosure, an implantable cardiac monitor (ICM) may be configured to be deployed subcutaneous, submuscular, or substernal at a position that enables the ICM to detect cardiac activity. In some cases, the ICM includes a first electrode that is secured relative to the ICM, a second electrode that is secured relative to the ICM and spaced from the first electrode and a third electrode that is secured relative to the ICM and spaced from the first electrode and the second electrode. The illustrative ICM may include a housing that is configured for subcutaneous, submuscular or substernal deployment and for supporting the first electrode, the second electrode and the third electrode. In some cases, the housing may include a body portion having a first end and a second end and a tail portion extending from the body portion to a tail end. The first electrode may be disposed adjacent the first end of the body portion, the second electrode may be disposed adjacent the second end of the body portion and the third electrode may be disposed adjacent the tail end of the tail portion of the housing. A controller may be disposed within the housing and may be operably coupled to the first electrode, the second electrode and the third electrode. In some cases, the controller may be configured to select a pair of the first electrode, the second electrode and the third electrode to establish a vector for sensing P-waves resulting from atrial contraction and to communicate information about the sensed P-waves to a second medical device. The second medical device may be, for example, an LCP or an SICD.

Alternatively or additionally to any of the embodiments above, the tail portion may be more flexible than the body portion.

Alternatively or additionally to any of the embodiments above, the body portion may include a hermitically sealed metallic enclosure that houses the controller, and the tail portion may include a polymeric body carrying the third electrode.

Alternatively or additionally to any of the embodiments above, the ICM may further include an antenna that is embedded in the polymeric body of the tail portion.

Alternatively or additionally to any of the embodiments above, the polymeric body of the tail portion may include a biocompatible polyurethane and/or a biocompatible polyethylene.

Alternatively or additionally to any of the embodiments above, the polymeric body may be secured relative to the hermitically sealed metallic enclosure.

Alternatively or additionally to any of the embodiments above, the ICM may further include an antenna that is carried by the tail portion.

Alternatively or additionally to any of the embodiments above, the antenna may be operatively coupled to the controller and is used to communicate with an external programmer.

Alternatively or additionally to any of the embodiments above, the controller may be configured to communicate information about the sensed P-waves to the second medical device via conducted communication using two of the first electrode, the second electrode and the third electrode.

Alternatively or additionally to any of the embodiments above, the controller may be configured to select which two of the first electrode, the second electrode and the third electrode to use for conducted communication with the second medical device.

Alternatively or additionally to any of the embodiments above, the controller may be configured to communicate information about the sensed P-waves to the second medical device via conducted communication using a pair of the first electrode, the second electrode and the third electrode.

Alternatively or additionally to any of the embodiments above, the controller may be configured to select which two of the first electrode, the second electrode and the third electrode to use for conducted communication with the second medical device.

Alternatively or additionally to any of the embodiments above, the ICM may further include an accelerometer disposed within the housing, wherein the controller is configured to communicate accelerometer information.

Alternatively or additionally to any of the embodiments above, the ICM may further include a heart sound sensor, wherein the controller is configured to communicate heart sound information.

Alternatively or additionally to any of the embodiments above, the controller may be configured to provide a signal to the second medical device that is suitable for the second medical device to determine a measure of minute ventilation and/or lung fluid volume.

In another example of the disclosure, an implantable cardiac monitor (ICM) may be configured to be deployed subcutaneous, submuscular or substernal at a position that enables the ICM to detect signs of cardiac activity. The ICM may include a housing, a first electrode that is secured relative to the housing, a second electrode that is secured relative to the housing and spaced from the first electrode, and a third electrode that is secured relative to the housing and is spaced from the first electrode and the second electrode. A controller may be disposed within the housing and may be operably coupled to the first electrode, the second electrode and the third electrode. The controller may be configured to select a pair of the first electrode, the second electrode and the third electrode for sensing cardiac electrical activity and to select a pair of the first electrode, the second electrode and the third electrode for communication with a second medical device.

Alternatively or additionally to any of the embodiments above, the controller may select which electrodes to use for sensing cardiac electrical activity based on which pair of electrodes provides a satisfactory sensing vector and to select which electrodes to use for communication with a second medical device based on which pair of electrodes provides a satisfactory communications vector with the second medical device.

Alternatively or additionally to any of the embodiments above, the controller may be configured to detect an atrial contraction using the pair of electrodes selected for sensing cardiac electrical activity, and to communicate information about a detected atrial contraction to the second medical device using the pair of electrodes selected for communication with the second medical device.

Alternatively or additionally to any of the embodiments above, the controller may be configured to select a different pair of electrodes for sensing cardiac electrical activity than for communication with the second medical device.

In another example of the disclosure, an implantable cardiac monitor (ICM) may be configured to be deployed subcutaneous, submuscular, or substernal at a position that enables the ICM to detect cardiac activity. The ICM includes a first electrode secured relative to the ICM, a second electrode secured relative to the ICM and spaced from the first electrode, and a third electrode secured relative to the ICM and spaced from the first electrode and the second electrode. A controller may be operably coupled to the first electrode, the second electrode and the third electrode. The ICM may include a housing that is configured for subcutaneous, submuscular or substernal deployment and to support the first electrode, the second electrode and the third electrode. The housing may include a body portion having a first end and a second end, wherein the body portion includes a hermetically sealed metallic enclosure that houses the controller, and a flexible tail portion extending from the body portion to a tail end, the flexible tail portion including a polymeric body carrying the third electrode. The controller may be configured to use a selected pair of the first electrode, the second electrode and the third electrode for sensing cardiac activity and to communicate information about the cardiac activity to a second medical device.

The above summary is not intended to describe each embodiment or every implementation of the present disclosure. Advantages and attainments, together with a more complete understanding of the disclosure, will become apparent and appreciated by referring to the following description and claims taken in conjunction with the accompanying drawings.

BRIEF DESCRIPTION OF THE DRAWINGS

The disclosure may be more completely understood in consideration of the following description of various illustrative embodiments in connection with the accompanying drawings, in which.

Figure 1:
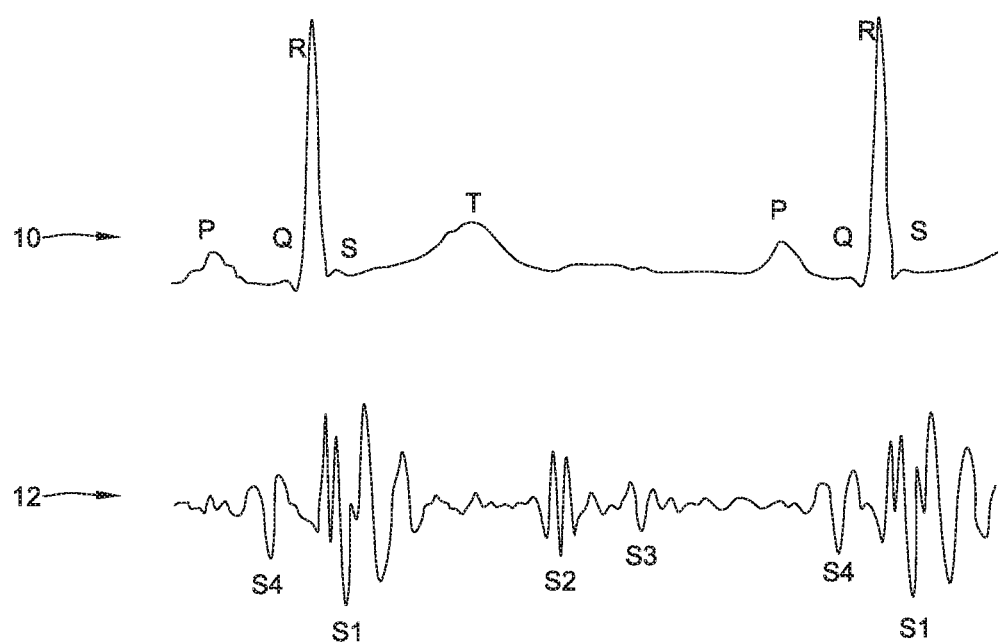
FIG. 1 is a graphical representation of an electrocardiogram (ECG) showing a temporal relationship between electrical signals of the heart and mechanical indications of contraction of the heart.

While the disclosure is amenable to various modifications and alternative forms, specifics thereof have been shown by way of example in the drawings and will be described in detail. It should be understood, however, that the intention is not to limit aspects of the disclosure to the particular illustrative embodiments described. On the contrary, the intention is to cover all modifications, equivalents, and alternatives falling within the spirit and scope of the disclosure.

DESCRIPTION

The following description should be read with reference to the drawings in which similar elements in different drawings are numbered the same. The description and the drawings, which are not necessarily to scale, depict illustrative embodiments and are not intended to limit the scope of the disclosure.

All numbers are herein assumed to be modified by the term "about", unless the content clearly dictates otherwise. The recitation of numerical ranges by endpoints includes all numbers subsumed within that range (e.g., 1 to 5 includes 1, 1.5, 2, 2.75, 3, 3.80, 4, and 5).

As used in this specification and the appended claims, the singular forms "a", "an", and "the" include the plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is contemplated that the feature, structure, or characteristic may be applied to other embodiments whether or not explicitly described unless clearly stated to the contrary.

A normal, healthy heart induces contraction by conducting intrinsically generated electrical signals throughout the heart. These intrinsic signals cause the muscle cells or tissue of the heart to contract in a coordinated manner. These contractions forces blood out of and into the heart, providing circulation of the blood throughout the rest of the body. Many patients suffer from cardiac conditions that affect the efficient operation of their hearts. For example, some hearts develop diseased tissue that no longer generate or efficiently conduct intrinsic electrical signals. In some examples, diseased cardiac tissue may conduct electrical signals at differing rates, thereby causing an unsynchronized and inefficient contraction of the heart. In other examples, a heart may generate intrinsic signals at such a low rate that the heart rate becomes dangerously low. In still other examples, a heart may generate electrical signals at an unusually high rate, even resulting in cardiac fibrillation. Implantable medical device are often used to treat such conditions by delivering one or more types of electrical stimulation therapy to the patient's heart.

FIG. 1 includes a portion of an electrocardiogram (ECG) 10 along with a heart sounds trace 12. As can be seen in the ECG 10, a heartbeat includes a P-wave that indicates atrial depolarization. A QRS complex, including a Q-wave, an R-wave and an S-wave, represents ventricular depolarization. A T-wave indicates repolarization of the ventricles. It will be appreciated that the ECG 10 may be detected by a variety of implanted or wearable cutaneous devices. A number of heart sounds may be detectable while the heart H beats. It will be appreciated that the heart sounds may be considered as on example of mechanical indications of the heart beating. Other illustrative mechanical indications may include, for example, endocardial acceleration or movement of a heart wall detected by an accelerometer in for example the LCP, acceleration or movement of a heart detected by an accelerometer in for example the SICD or ICM, a pressure, pressure change, or pressure change rate in a chamber of the heart H detected by a pressure sensor of the LCP or other intracardiac device, acoustic signals caused by heart movements detected by an acoustic sensor (e.g. accelerometer, microphone, etc.) in the LCP, SICD, ICM and/or other device, and/or other suitable indication of a heart chamber beating.

An electrical signal typically instructs a portion of the heart H to contract, and then there is a corresponding mechanical indication. In some cases, there may be a first heart sound that is denoted S1 and that is produced by vibrations generated by closure of the mitral and tricuspid valves during a ventricle contraction, a second heart sound that is denoted S2 and that is produced by closure of the aortic and pulmonary valves, a third heart sound that is denoted S3 and that is an early diastolic sound caused by the rapid entry of blood from the right atrium RA into the right ventricle RV and from the left atrium LA into the left ventricle LV, and a fourth heart sound that is denoted S4 and that is a late diastolic sound corresponding to late ventricular filling during an active atrial contraction.

Because the heart sounds are a result of cardiac muscle contracting or relaxing in response to an electrical signal, it will be appreciated that there is a delay between the electrical signal, indicated by the ECG 10, and the corresponding mechanical indication, indicated in the example shown by the heart sounds trace 12. For example, the P-wave of the ECG 10 is an electrical signal triggering an atrial contraction. The S4 heart sound is the mechanical signal caused by the atrial contraction. In some cases, it may be possible to use this relationship between the P-wave and the S4 heart sound. For example, if one of these signals may be detected, the relationship can be used as a timing mechanism to help search for the other. For example, if the P-wave can be detected, a window following the P-wave can be defined and searched in order to find and/or isolate the corresponding S4 heart sound. In some cases, detection of both signals may be an indication of an increased confidence level in a detected atrial contraction. In some cases, detection of either signal may be sufficient to identify an atrial contraction. The identity of an atrial contraction may be used to identify an atrial contraction timing fiducial (e.g. a timing marker of the atrial contraction).

Figure 2:
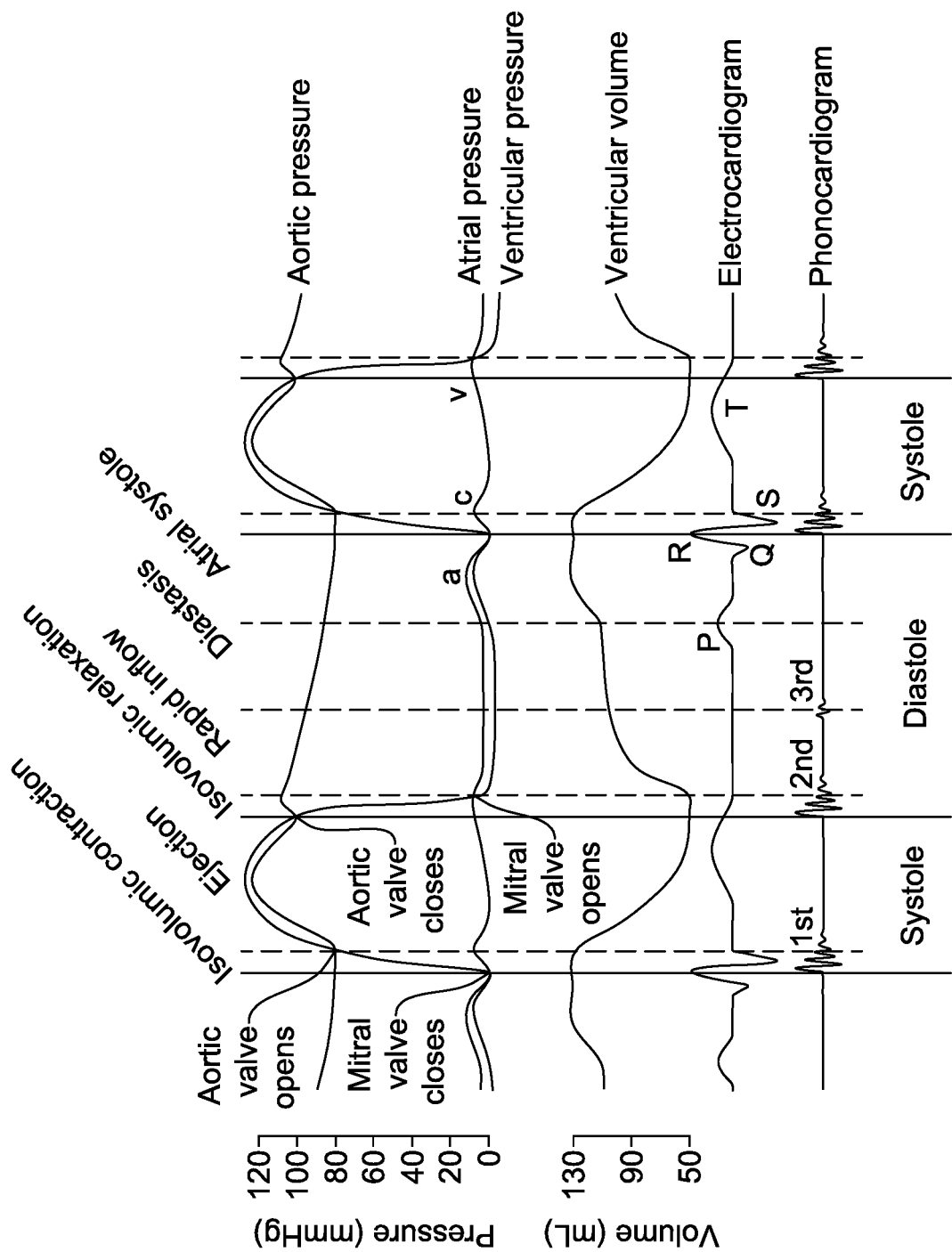
FIG. 2 is a graph showing an example ECG, various pressures, various volumes, and various heart sounds over two consecutive heart beats.

In some cases, the relationship of certain electrical signals and/or mechanical indications may be used to predict the timing of other electrical signals and/or mechanical indications within the same heartbeat. Alternatively, or in addition, the timing of certain electrical signals and/or mechanical indications corresponding to a particular heartbeat may be used to predict the timing of other electrical signals and/or mechanical indications within a subsequent heartbeat. It will be appreciated that as the heart H undergoes a cardiac cycle, the blood pressures and blood volumes within the heart H will vary over time. FIG. 2 illustrates how these parameters typically match up with the electrical signals and corresponding mechanical indications in a healthy heart H.

FIG. 2 is a graph showing an example ECG, various pressures, various volumes, and various heart sounds over two consecutive beats of a heart H. More specifically, FIG. 2 shows an illustrative example of the aortic pressure, left ventricular pressure, left atrial pressure, left ventricular volume, an electrocardiogram (ECG or egram), and heart sounds of the heart H over two consecutive heart beats. A cardiac cycle may begin with diastole, and the mitral valve opens. The ventricular pressure falls below the atrial pressure, resulting in the ventricular filling with blood. During ventricular filling, the aortic pressure slowly decreases as shown. During systole, the ventricle contracts. When ventricular pressure exceeds the atrial pressure, the mitral valve closes, generating the S1 heart sound. Before the aortic valve opens, an isovolumetric contraction phase occurs where the ventricle pressure rapidly increases but the ventricle volume does not significantly change. Once the ventricular pressure equals the aortic pressure, the aortic valve opens and the ejection phase begins where blood is ejected from the left ventricle into the aorta. The ejection phase continues until the ventricular pressure falls below the aortic pressure, at which point the aortic valve closes, generating the S2 heart sound. At this point, the isovolumetric relaxation phase begins and ventricular pressure falls rapidly until it is exceeded by the atrial pressure, at which point the mitral valve opens and the cycle repeats. Cardiac pressure curves for the pulmonary artery, the right atrium, and the right ventricle, and the cardiac volume curve for the right ventricle, may be similar to those illustrated in FIG. 2. In many cases, the cardiac pressure in the right ventricle is lower than the cardiac pressure in the left ventricle.

Figure 3:
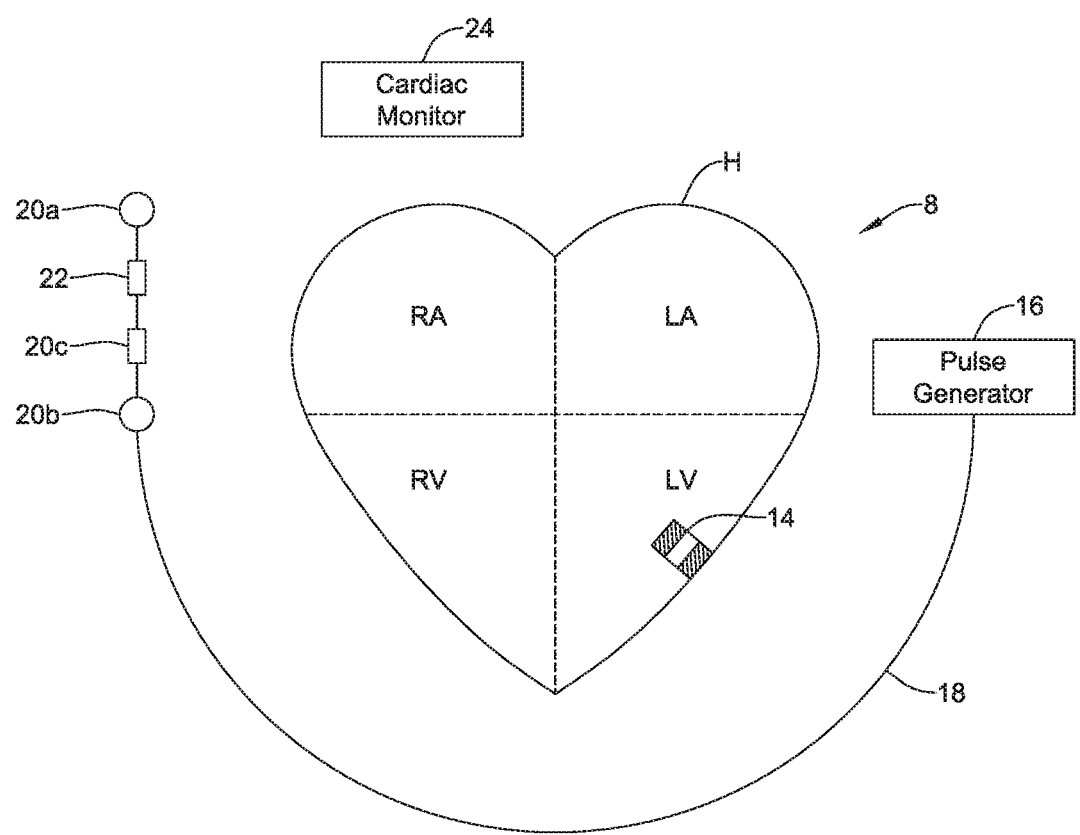
FIG. 3 is a schematic diagram of an illustrative system including an LCP and another medical device, in accordance with an example of the disclosure.

FIG. 3 shows an illustrative medical device system 8 that includes several different implantable devices that may be implanted in and/or near a heart H. As can be seen, the heart H includes a right atrium RA, a left atrium LA, a right ventricle RV and a left ventricle LV. In FIG. 3, an LCP 14 is disposed within the LV and is attached to the ventricular wall. A pulse generator 16 is shown coupled to a lead 18 having one or more electrodes 20a, 20b, 20c. In some cases, the pulse generator 16 may be part of a subcutaneous implantable cardioverter-defibrillator (SICD), and the one or more electrodes 20a, 20b, 20c may be positioned subcutaneously and exterior of the sternum. In some cases, the one or more electrodes 20a, 20b, 20c may be placed inside of the chest cavity but outside of the heart, such as just interior of the sternum. In some cases, the LCP 14 may communicate with the subcutaneous implantable cardioverter-defibrillator (S-ICD). In some cases, the lead 18 may include an accelerometer 22 that may, for example, be configured to sense vibrations that may be indicative of heart sounds and/or other movement of the heart, chest cavity and the like.

In some cases, the LCP 14 may be in the right ventricle RV, right atrium RA, left ventricle LV or left atrium LA of the heart H, as desired. In some cases, more than one LCP 14 may be implanted. For example, one LCP may be implanted in the right ventricle RV and another may be implanted in the right atrium RA. In another example, one LCP may be implanted in the right ventricle RV and another may be implanted in the left ventricle LV. In yet another example, one LCP may be implanted in each of the chambers of the heart H.

In some cases, the medical device system 8 may include an implantable cardiac monitor (ICM) 24. While one ICM 24 is shown, it will be appreciated that in some cases multiple ICMs may be implanted. In some cases, the ICM 24 may be implanted at a subcutaneous position, a submuscular position or a substernal position. In some cases, the ICM 24 may instead be disposed within the patient's vascular system at a location where the ICM 24 may sense aspects of the cardiac cycle. For example, the ICM 24 may be deployed within the internal thoracic vein. It will be appreciated that this location is merely illustrative. In some cases, the exact location may be driven at least in part by what particular aspects of the cardiac cycle the ICM 24 is configured or otherwise intended to sense. For example, if the ICM 24 is intended to sense atrial activity, such as but not limited to detecting P-waves, the ICM 24 may be implanted at a location relatively close to the top of the heart H in order to place the ICM 24 at a location where P-waves may be more easily detected. If the ICM 24 is intended to sense heart sounds, the ICM 24 may be implanted at a location relatively close to the ventricles of the heart H. If the ICM 24 is intended to sense respiration, the ICM 24 may be implanted at a pectoral or other location that provides a good vector across the lungs of the patient. These are just examples.

In some cases, one or more ICMs 24 may be implanted at particular locations to better sense localized cardiac activity, as discussed above. In some cases, using one or more ICMs 24, which include particular electrode combinations and/or various sensors configured to sense cardiac electrical activity and/or to detect mechanical indications of cardiac activity, may enable other devices such as the LCP 14 to be made smaller, as the LCP 14 may not need to include particular sensors, for example, if the ICM 24 provides the information that would otherwise be provided by one or more sensors on board the LCP 14. This may be of particular advantage, for example, if there are multiple LCPs implanted within the heart H. In addition, or alternatively, using one or more ICMs 24 may enable other devices such as the LCP 14 to use less power, as the LCP 14 may not need to sense for particular signals or events if the ICM 24 provides the desired information. In addition, or alternatively, using one or more ICMs 24 may enable other devices such as the LCP 14 to monitor signals that are otherwise hard to sense from the location of the other device. For example, an LCP 14 implanted in the left ventricle may find it difficult to sense the P-wave emanating from the atrium.

Figure 4:
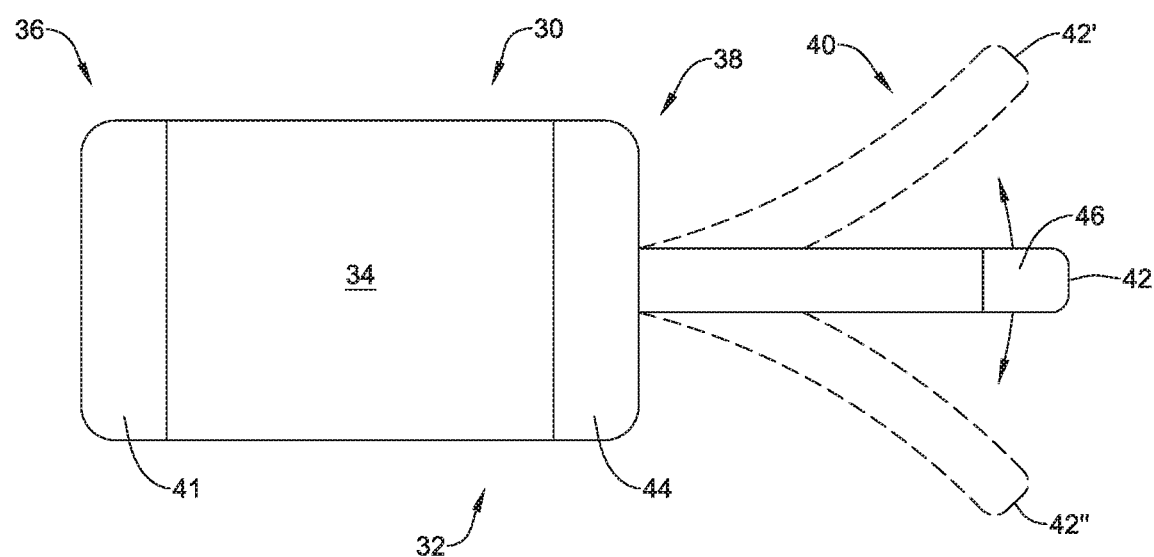
FIG. 4 is a schematic view of an illustrative implantable cardiac monitor (ICM) in accordance with an example of the disclosure.

FIG. 4 is a schematic view of an illustrative implantable cardiac monitor (ICM) 30 that may, for example, be considered as being an example of the ICM 24 (FIG. 3). The illustrative ICM 30 includes a housing 32 that may be configured for subcutaneous, submuscular or substernal deployment. In some cases, the housing 32 may include a body portion 34 that extends from a first end 36 to a second end 38. In some cases, the housing 32 may include a tail portion 40 that extends from the body portion 34 to a tail end 42. In some cases, the tail portion 40 may be flexible, as indicated by the phantom tail portions including a tail end 42' and a tail end 42". In some cases, the body portion 34 may be a hermitically sealed metallic enclosure that encloses a controller, as will be illustrated in subsequent Figures. In some cases, the tail portion 40 may include a polymeric material and may be made flexible. In some cases, for example, the tail portion 40 may include or otherwise be formed of a biocompatible polyurethane and/or a biocompatible polyethylene. The tail portion 40 may be secured relative to the hermitically sealed metallic enclosure. The tail portion 40 may be flexible such that the tail end 42 can be moved about and implanted in a desired configuration.

In some cases, the ICM 30 may include a first electrode 41 that is secured relative to the ICM 30, a second electrode 44 that is secured relative to the ICM 30 and is spaced from the first electrode 41, and a third electrode 46 that is secured relative to the ICM 30 and is spaced from the first electrode 41 and the second electrode 44. In some cases, the first electrode 41 may be disposed adjacent the first end 36 of the body portion 34. In some cases, the second electrode 44 may be secured adjacent the second end 38 of the body portion 34. The third electrode 46 may, for example, be disposed adjacent the tail end 42 of the tail portion 40. By moving the tail end 42 off axis relative to the other two fixed electrodes, the three electrodes 41, 44 and 46 may be oriented non co-axially when implanted. When so provided, the ability to select two of the three electrodes for sensing and/or communication provide a number of different off-axis sensing and/or communication vectors to choose from.

Figure 5:
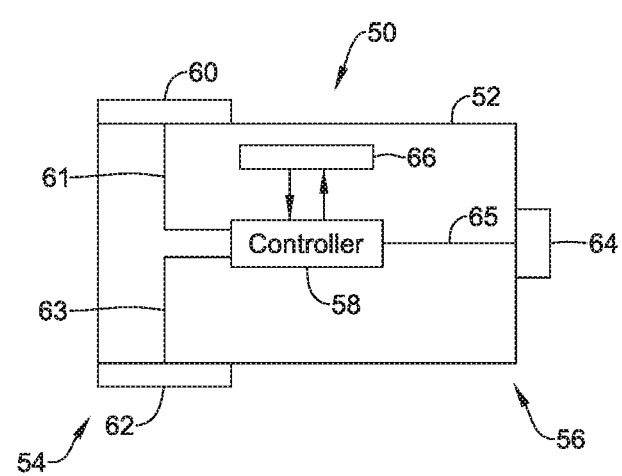
FIG. 5 is a schematic view of an illustrative implantable cardiac monitor (ICM) in accordance with an example of the disclosure.

FIG. 5 is a schematic view of an illustrative implantable cardiac monitor (ICM) 50 that may, for example, be considered as being an example of the ICM 24 (FIG. 3). The illustrative ICM 50 includes a housing 52 that may be configured for subcutaneous, submuscular or substernal deployment. In some cases, the housing 52 may extend from a first end 54 to a second end 56 and may house a controller 58. The controller 58 may be operably coupled with a first electrode 60, a second electrode 62 and a third electrode 64 via electrical connections 61, 63 and 65, respectively. In some cases, the ICM 50 may include fewer electrodes. In some cases, the ICM 50 may include additional electrodes (not illustrated). As shown, the first electrode 60 and the second electrode 62 are disposed at or near the first end 54 of the housing 52 while the third electrode 64 is disposed at or near the second end 56 of the housing 52. It will be appreciated that the relative locations of the electrodes 60, 62, 64 are merely illustrative.

In some cases, the controller 58 may be configured to select a pair of electrodes of the first electrode 60, the second electrode 62 and the third electrode 64 to use for sensing cardiac activity. In an example, the controller 58 may be configured for selecting a pair of electrodes of the first electrode 60, the second electrode 62 and the third electrode 64 to use for sensing P-waves resulting from atrial contraction. The controller 58 may, for example, use the first electrode 60 and the second electrode 62 as a pair, or the first electrode 60 and the third electrode 64 as a pair, or the second electrode 62 and the third electrode 64 for sensing cardiac electrical activity. In some cases, the controller 58 may be configured to communicate information about the sensed cardiac electrical activity, including but not limited to sensed P-waves to a second medical device such as, for example, the LCP 14 or the pulse generator 16 shown in FIG. 3.

In some cases, the controller 58 may be configured to communicate information about the sensed P-waves to the second medical device via conducted communication using two of the first electrode 60, the second electrode 62 and the third electrode 64. In some cases, the controller 58 may be configured to select which two of the first electrode 60, the second electrode 62 and the third electrode 64 to use for conducted communication with the second medical device. In some cases, the controller 58 may be configured to communicate information about the sensed P-waves to the second medical device via conducted communication using a pair of the first electrode 60, the second electrode 62 and the third electrode 64.

The controller 58 may, for example, be configured to select which two of the first electrode 60, the second electrode 62 and the third electrode 64 to use for conducted communication with the second medical device. In some cases, the controller 58 may be configured to select which electrodes of the electrodes 60, 62, 64 to use for communication with a second medical device based on which pair of electrodes provides a satisfactory communications vector with the second medical device. In some cases, the controller 58 may select a first electrode pair for sensing and a different electrode pair for communication. In some cases, the controller 58 may select the same electrode pair for both sensing and communication. As an example, if the ICM 50 is being used to sense atrial activity such as sensed P-waves, the controller 58 may be configured to detect an atrial contraction using the pair of electrodes selected for sensing cardiac electrical activity and to communicate information about the detected atrial contraction to the second medical device using the pair of electrodes selected for communication with the second medical device.

In some cases, the ICM 50 may include a sensor 66 that is operably coupled with the controller 58. In some instances, the sensor 66 may be or otherwise include an accelerometer, and the controller 58 may be configured to communicate accelerometer information. In some instances, the sensor 66 may be or otherwise include a heart sound sensor, and controller 58 may be configured to communicate heart sound information. In some cases, the controller 58 may be configured to provide a signal to the second medical device that is suitable for the second medical device to determine a measure of minute ventilation and/or lung fluid volume.

Figure 6:
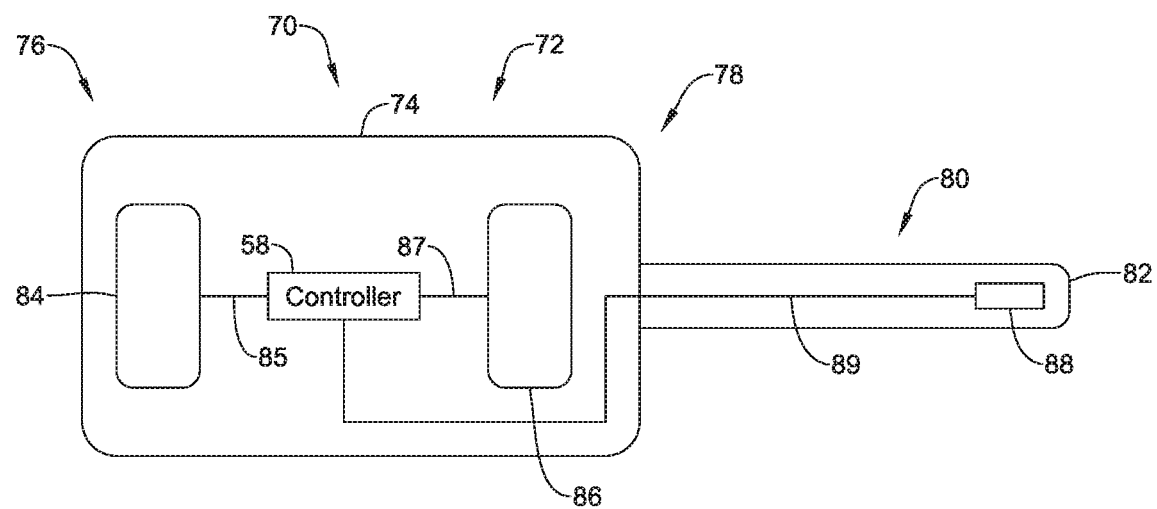
FIG. 6 is a schematic view of an illustrative implantable cardiac monitor (ICM) in accordance with an example of the disclosure.

FIG. 6 is a schematic view of an illustrative implantable cardiac monitor (ICM) 70 that may, for example, be considered as being an example of the ICM 24 (FIG. 3). The illustrative ICM 70 includes a housing 72 that may be configured for subcutaneous, submuscular or substernal deployment. In some cases, the housing 72 may include a body portion 74 that extends from a first end 76 to a second end 78. The housing 72 may include a tail portion 80 that extends from the body portion 74 to a tail end 82. In some cases, the tail portion 80 may be flexible. In some cases, the body portion 74 may be a hermetically sealed metallic enclosure that encloses the controller 58. In some cases, the tail portion 80 may be formed of a polymeric material. In some cases, for example, the tail portion 80 may include or otherwise be formed of a biocompatible polyurethane and/or a biocompatible polyethylene. The tail portion 80 may be secured relative to the hermetically sealed metallic enclosure, for example.

In some cases, the ICM 70 may include a first electrode 84 that is secured relative to the ICM 70, a second electrode 86 that is secured relative to the ICM 70 and is spaced from the first electrode 84, and a third electrode 88 that is secured relative to the ICM 70 and is spaced from the first electrode 84 and the second electrode 86. In some cases, the first electrode 84 may be disposed adjacent the first end 76 of the body portion 74. In some cases, the second electrode 86 may be secured adjacent the second end 78 of the body portion 74. The third electrode 88 may, for example, be disposed adjacent the tail end 82 of the tail portion 80. In some cases, the controller 58 may be operably coupled with the first electrode 84, the second electrode 86 and the third electrode 88 via electrical connectors 85, 87 and 89, respectively.

Figure 7:
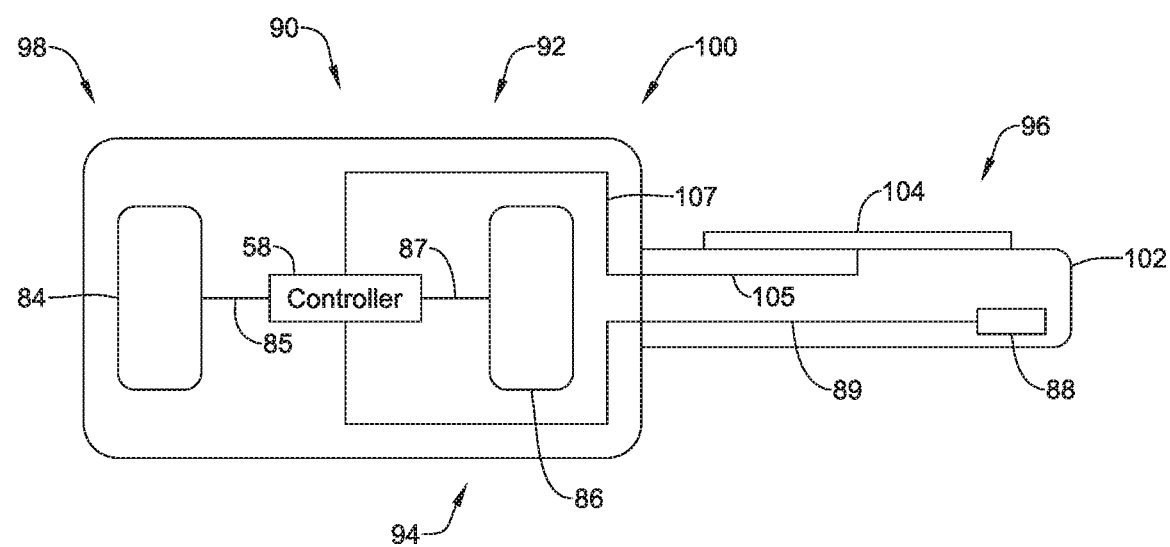
FIG. 7 is a schematic view of an illustrative implantable cardiac monitor (ICM) in accordance with an example of the disclosure.

FIG. 7 is a schematic view of an illustrative implantable cardiac monitor (ICM) 90 that may, for example, be considered as being an example of the ICM 24 (FIG. 3). The illustrative ICM 90 includes a housing 92 that may be configured for subcutaneous, submuscular or substernal deployment. In some cases, the housing 92 may include a body portion 94 and a tail portion 96. The body portion 94 extends from a first end 98 to a second end 100. The tail portion 96 extends from the body portion 94 to a tail end 102. In some cases, the tail portion 96 may be flexible. In some cases, the body portion 94 may be a hermetically sealed metallic enclosure that encloses the controller 58. In some cases, the tail portion 96 may be formed of a polymeric material. In some cases, for example, the tail portion 96 may include or otherwise be formed of a biocompatible polyurethane and/or a biocompatible polyethylene. The tail portion 96 may be secured relative to the hermetically sealed metallic enclosure, for example.

In some cases, the ICM 90 may include the first electrode 84, the second electrode 86 and the third electrode 88 that are operably coupled to the controller 58 via the electrical connectors 85, 87 and 89, respectively. In some cases, the ICM 90 may include an antenna 104 that is operably coupled to the controller 58 via an electrical connector 105. The antenna 104 may, for example, be carried by the tail portion 96. In some cases, the antenna 104 may be secured to an outer surface of the tail portion 96, or may be embedded in the flexible polymeric material of the tail portion 96. In some cases, the antenna may be an RF antenna, an inductive antenna (i.e. coil), and/or any other suitable antenna suitable for communication with a second medical device. In some cases, the antenna 104 may be used to communicate with an external programmer.

Figure 8:
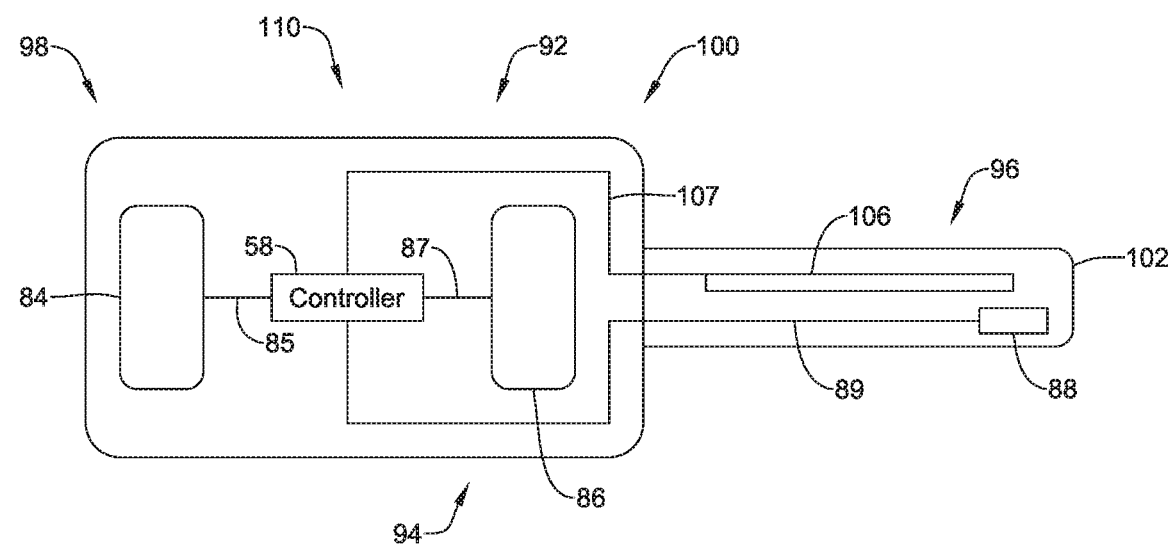
FIG. 8 is a schematic view of an illustrative implantable cardiac monitor (ICM) in accordance with an example of the disclosure.

FIG. 8 is a schematic view of an illustrative implantable cardiac monitor (ICM) 110 that may, for example, be considered as being an example of the ICM 24 (FIG. 3). The illustrative ICM 110 includes a housing 92 that may be configured for subcutaneous, submuscular or substernal deployment. In some cases, the housing 92 may include a body portion 94 and a tail portion 96. The body portion 94 extends from a first end 98 to a second end 100. The tail portion 96 extends from the body portion 94 and to a tail end 102. In some cases, the tail portion 96 may be flexible. In some cases, the body portion 94 may be a hermitically sealed metallic enclosure that encloses the controller 58. In some cases, the tail portion 96 may be formed of a polymeric material. In some cases, for example, the tail portion 96 may include or otherwise be formed of a biocompatible polyurethane and/or a biocompatible polyethylene. The tail portion 96 may be secured relative to the hermitically sealed metallic enclosure, for example.

In some cases, the ICM 110 may include the first electrode 84, the second electrode 86 and the third electrode 88 that are operably coupled to the controller 58 via the electrical connectors 85, 87 and 89, respectively. In some cases, the ICM 110 may include an antenna 106 that is embedded in the flexible polymeric material of the tail portion 96 and is operably coupled to the controller 58 via an electrical connector 107. In some cases, the antenna may be an RF antenna, an inductive antenna (i.e. coil), and/or any other suitable antenna suitable for communication with a second medical device. In some cases, the antenna 106 may be used to communicate with an external programmer.

Figure 9:
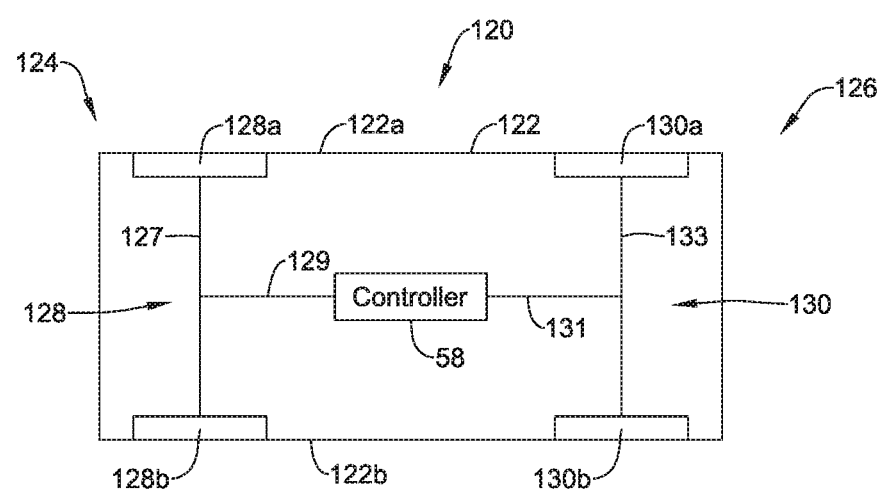
FIG. 9 is a schematic view of an illustrative implantable cardiac monitor (ICM) in accordance with an example of the disclosure.

FIG. 9 is a schematic view of an illustrative implantable cardiac monitor (ICM) 120 that may, for example, be considered as being an example of the ICM 24 (FIG. 3). The illustrative ICM 120 includes a housing 122 that may be configured for subcutaneous, submuscular or substernal deployment and that includes a first side 122a and a second opposing side 122b. In some cases, the housing 122 may extend from a first end 124 to a second end 126 and may house the controller 58 within the housing 122. In some cases, the ICM 120 may include a first electrode 128 that is disposed at or near the first end 124 of the housing 122 and a second electrode 130 that is disposed at or near the second end 126 of the housing 122. It will be appreciated that in some instances, the ICM 120 may be inserted in an orientation that is 180 degrees from its final deployment orientation. In some cases, for example, there may be a desire to test a possible location before inverting the ICM 120 for its final deployment in the patient's body.

Accordingly, the first electrode 128 may include a first electrode portion 128a that is disposed on the first side 122a and a second electrode portion 128b that is disposed on the opposing second side 122b. Similarly, the second electrode 130 may include a first electrode portion 130a that is disposed on the first side 122a and a second electrode portion 130b that is disposed on the opposing second side 122b. Accordingly, the controller 58 is configured to be electrically coupled to the first electrode 128 and the second electrode 130, with the first electrode 128 and the second electrode 130 in contact with a desired tissue region independent of orientation of the first side 122a and the second side 122b. For example, if the first side 122a is in contact with the desired tissue location prior to inversion, the first electrode portions 128a, 130a are in contact with the desired tissue location. After device inversion, the second side 122b would be in contact with the desired tissue location, and thus the second electrode portions 128b, 130b would be in contact with the desired tissue location.

Figure 10:
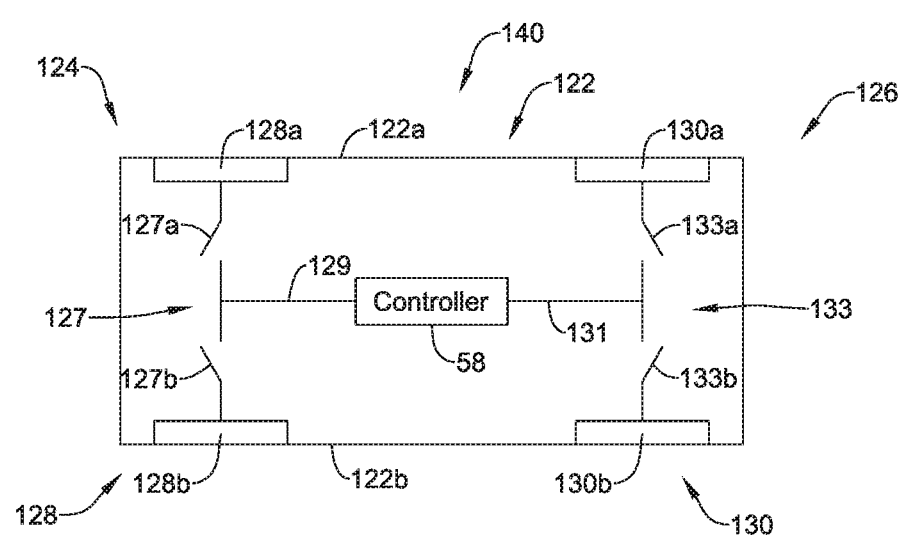
FIG. 10 is a schematic view of an illustrative implantable cardiac monitor (ICM) in accordance with an example of the disclosure.

FIG. 10 is a schematic view of an illustrative implantable cardiac monitor (ICM) 140 that may, for example, be considered as being an example of the ICM 24 (FIG. 3). The illustrative ICM 140 includes a housing 122 that may be configured for subcutaneous, submuscular or substernal deployment and that includes a first side 122a and an opposing second side 122b. In some cases, the housing 122 may extend from a first end 124 to a second end 126 and may house the controller 58 within the housing 122. In some cases, the ICM 120 may include a first electrode 128 that is disposed at or near the first end 124 of the housing 122 and a second electrode 130 that is disposed at or near the second end 126 of the housing 122. It will be appreciated that in some instances, the ICM 140 may be inserted in an orientation that is 180 degrees from its final deployment orientation. In some cases, for example, there may be a desire to test a possible location before inverting the ICM 140 for its final deployment.

Accordingly, the first electrode 128 may include a first electrode portion 128a that is disposed on the first side 122a, and a second electrode portion 128b that is disposed on the opposing second side 122b. Similarly, the second electrode 130 may include a first electrode portion 130a that is disposed on the first side 122a, and a second electrode portion 130b that is disposed on the opposing second side 122b. Accordingly, the controller 58 may be able to be electrically coupled to the first electrode 128 and the second electrode 130, with the first electrode 128 and the second electrode 130 in contact with a desired tissue location independent of orientation or the first side 122a and the second side 122b. For example, if the first side 122a is in contact with the desired tissue location prior to inversion of the ICM 140, the first electrode portions 128a, 130a are in contact with the desired tissue location. After device inversion, the second side 122b will be in contact with the desired tissue location, and thus the second electrode portions 128b, 130b will be in contact with the desired tissue location.

In some cases, there may be a desire to not electrically couple the first electrode portion 128a to the second electrode portion 128b, or to not electrically couple the first electrode portion 130a to the second electrode portion 130b. While the first electrode 128 is coupled to the controller 58 via electrical connectors 127 and 129, it can be seen that the electrical connector 127 schematically includes a switch 127a and a switch 127b. While shown separate from the controller 58, it will be appreciated that the switches 127a and 127b may be incorporated into the controller 58 and thus may be under the control of the controller 58. Similarly, the electrical connector 133 coupling the second electrode 130 to the controller 58 may include a switch 133a and a switch 133b. In some cases, the controller 58 can selectively electrically connect or disconnect to any of the first electrode portion 128a, the second electrode portion 128b, the first electrode portion 130a and/or the second electrode portion 130b.

In one example, when the ICM 140 is implanted subcutaneously and is intended to sense P-waves of the heart, it may be desirable to connect the electrode portions that face away from the heart to the controller 58 for sensing P-waves, and disconnect and even ground the electrode portions that face toward the heart. In some instances, muscle activity adjacent the side of the ICM 140 facing the heart can introduce unwanted noise at the electrode portions that face toward the heart.

Figure 11:
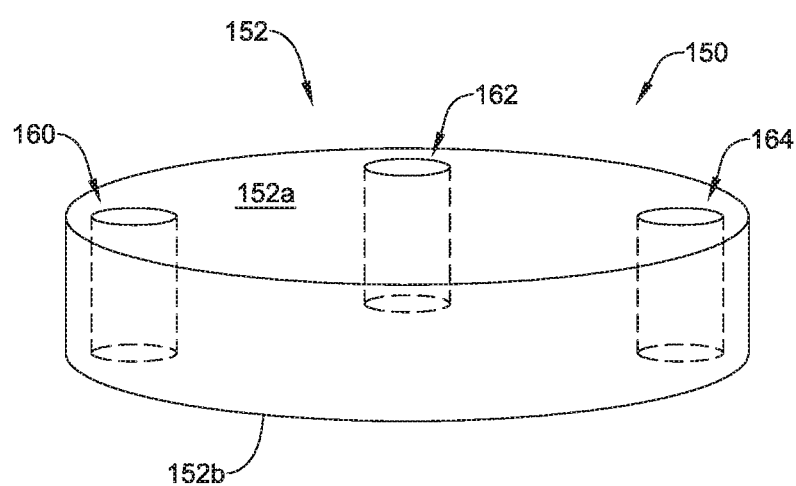
FIG. 11 is a schematic view of an illustrative implantable cardiac monitor (ICM) in accordance with an example of the disclosure.

FIG. 11 is a schematic view of an illustrative implantable cardiac monitor (ICM) 150 that may, for example, be considered as being an example of the ICM 24 (FIG. 3). The illustrative ICM 150 includes a housing 152 that may be configured for subcutaneous, submuscular or substernal deployment and that includes a first side 152*a* and a second side 152*b*. In some cases, the housing 152 may have an ovoid or circular profile. In some cases, the first side 152*a* may include a first electrode 160, a second electrode 162 and a third electrode 164. In some cases, the ICM 150 may include fewer electrodes. In some cases, the ICM 150 may include additional electrodes. In some cases, the first electrode 160 may include a first electrode portion 160*a* on the first side 152*a* and a second electrode portion 160*b* on the opposing second side 152*b*. The second electrode 162 may include a first electrode portion 162*a* on the first side 152*a* and a second electrode 162*b* on the opposing second side 152*b*. The third electrode 164 may include a first electrode portion 164*a* on the first side 152*a* and a second electrode portion 164*b* on the opposing second side 152*b*. It is contemplated that the first electrode 160, the second electrode 162 and the third electrode 164 may optionally be individually switched into or out of electrical contact with the controller 58 (not shown).

Figure 12:
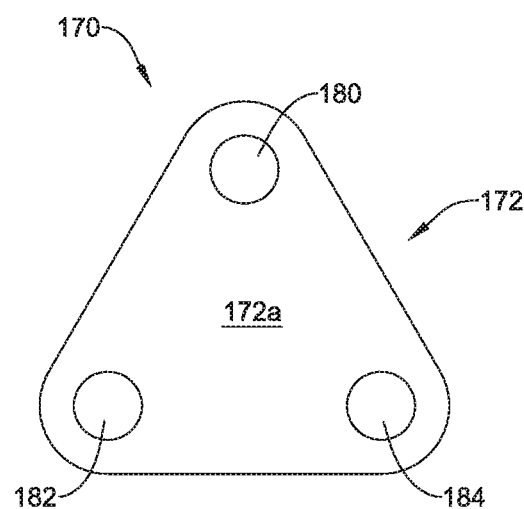
FIG. 12 is a schematic view of an illustrative implantable cardiac monitor (ICM) in accordance with an example of the disclosure.
Figure 13:
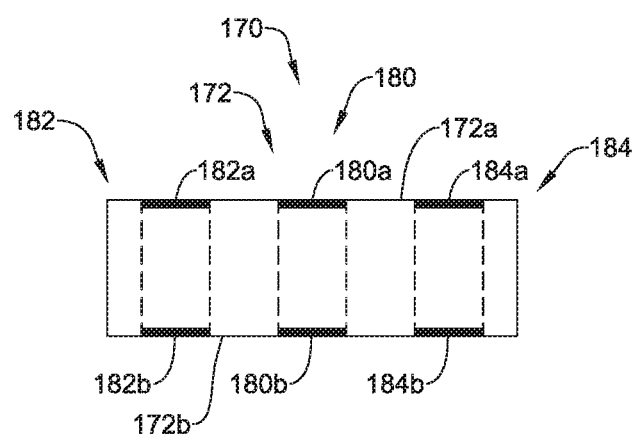
FIG. 13 is a side view of the ICM of FIG. 12.

FIG. 12 is a schematic view of an illustrative implantable cardiac monitor (ICM) 170 and FIG. 13 is a side view thereof that may, for example, be considered as being an example of the ICM 24 (FIG. 3). The illustrative ICM 170 includes a housing 172 that may be configured for subcutaneous, submuscular or substernal deployment and that includes a first side 172*a* and an opposing second side 172*b*. In some cases, the housing 172 may have a triangular shape, sometimes with rounded corners. In some cases, the ICM 170 may include a first electrode 180, a second electrode 182 and a third electrode 184. In some cases, the ICM 170 may include fewer electrodes. In some cases, the ICM 170 may include additional electrodes. In some cases, the first electrode 180 may include a first electrode portion 180*a* on the first side 172*a* and a second electrode portion 180*b* on the opposing second side 172*b*. The second electrode 182 may include a first electrode portion 182*a* on the first side 172*a* and a second electrode 182*b* on the opposing second side 172*b*. The third electrode 184 may include a first electrode portion 184*a* on the first side 172*a* and a second electrode portion 184*b* on the opposing second side 172*b*. The first electrode 180, the second electrode 182 and the third electrode 184 may each be positioned adjacent a corresponding corner of the triangular shaped housing 172. In some cases, the first electrode 180, the second electrode 182 and the third electrode 184 may optionally be individually switched into or out of electrical contact with the controller 58 (not shown).

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments.

What is claimed is:

1. An implantable cardiac monitor (ICM) configured to be deployed subcutaneous, submuscular, or substernal at a position that enables the ICM to detect cardiac activity of a patient's heart but the ICM is not configured to provide therapy to the patient's heart, the ICM comprising:
   a first electrode;
   a second electrode spaced from the first electrode;
   a third electrode spaced from the first electrode and the second electrode;
   a housing that is configured for subcutaneous, submuscular or substernal deployment and to support the first electrode, the second electrode and the third electrode, the housing comprising:
      a body portion having a first end and a second end;
      a tail portion extending from the body portion to a tail end;
   the first electrode disposed adjacent the first end of the body portion;
   the second electrode disposed adjacent the second end of the body portion;
   the third electrode disposed adjacent the tail end of the tail portion;
   a controller disposed within the housing and operably coupled to the first electrode, the second electrode and the third electrode;
   the controller configured to select a pair of the first electrode, the second electrode and the third electrode to use for sensing P-waves resulting from an atrial contraction; and
   the controller configured to communicate via wireless communication an atrial contraction timing fiducial based on a sensed P-wave to a second medical device that receives and uses the communicated atrial contraction timing fiducial to deliver a therapy to the patient's heart.

2. The ICM of claim 1, wherein the tail portion is more flexible than the body portion.

3. The ICM of claim 2, wherein the body portion comprises a hermetically sealed metallic enclosure that houses the controller, and the tail portion comprises a polymeric body carrying the third electrode.

4. The ICM of claim 3, further comprises an antenna wherein the antenna is embedded in the polymeric body of the tail portion.

5. The ICM of claim 3, wherein the polymeric body of the tail portion comprises a biocompatible polyurethane and/or a biocompatible polyethylene.

6. The ICM of claim 3, wherein the polymeric body is secured relative to the hermetically sealed metallic enclosure.

7. The ICM of claim 2, further comprises an antenna wherein the antenna is carried by the tail portion.

8. The ICM of claim 7, wherein the antenna is operatively coupled to the controller and is used to communicate with an external programmer.

9. The ICM of claim 1, wherein the second medical device is a subcutaneous implantable cardioverter-defibrillator (SICD), and the controller is configured to communicate information about the sensed P-waves to the SICD via conducted communication using two of the first electrode, the second electrode and the third electrode.

10. The ICM of claim 9, wherein the controller is configured to select which two of the first electrode, the second electrode and the third electrode to use for conducted communication with the SICD.

11. The ICM of claim 1, wherein
   the second medical device is a leadless cardiac pacemaker (LCP), and the controller is configured to communicate information about the sensed P-waves to the LCP via conducted communication using a pair of the first electrode, the second electrode and the third electrode.

12. The ICM of claim 11, wherein the controller is configured to select which two of the first electrode, the second electrode and the third electrode to use for conducted communication with the LCP.

13. The ICM of claim 1, further comprising an accelerometer disposed within the housing, wherein the controller is configured to communicate accelerometer information.

14. The ICM of claim 1, further comprising a heart sound sensor, wherein the controller is configured to communicate heart sound information.

15. An implantable cardiac monitor (ICM) configured to be deployed subcutaneous, submuscular or substernal at a position that enables the ICM to detect signs of cardiac activity, the ICM comprising:
    a housing having a first major housing side extending substantially parallel with an opposing second major housing side and a minor side wall extending therebetween;
    a first electrode secured relative to the housing, the first electrode having a first electrode portion on the first major housing side and a second electrode portion spaced from the first electrode portion of the first electrode and on the opposing second major housing side;
    a second electrode secured relative to the housing and spaced from the first electrode, the second electrode having a first electrode portion on the first major housing side and a second electrode portion spaced from the first electrode portion of the second electrode and on the opposing second major housing side;
    a third electrode secured relative to the housing and spaced from the first electrode and the second electrode, the third electrode having a first electrode portion on the first major housing side and a second electrode portion spaced from the first electrode portion of the third electrode and on the opposing second major housing side;
    a controller disposed within the housing and operably coupled to the first electrode, the second electrode and the third electrode;
    the controller configured to select a pair of the first electrode, the second electrode and the third electrode for sensing cardiac electrical activity; and
    the controller configured to select a pair of the first electrode, the second electrode and the third electrode for communication with a second medical device;
    wherein the first electrode, the second electrode and the third electrode permit testing of a possible location for deployment of the ICM before inverting the ICM into its desired deployment orientation.

16. The ICM of claim 15, wherein the pair of the first electrode, the second electrode and the third electrode selected for sensing cardiac electrical activity is the same as the pair of the first electrode, the second electrode and the third electrode selected for communication with the second medical device.

17. The ICM of claim 15, wherein the controller is configured to detect an atrial contraction using the pair of electrodes selected for sensing cardiac electrical activity, and is further configured to communicate an atrial contraction timing fiducial based on a detected atrial contraction to the second medical device using the pair of electrodes selected for communication with the second medical device.

18. The ICM of claim 15, wherein the controller is configured to select a different pair of electrodes for sensing cardiac electrical activity than for communication with the second medical device.

19. An implantable cardiac monitor (ICM) configured to be deployed subcutaneous, submuscular, or substernal at a position that enables the ICM to detect cardiac activity, the ICM comprising:
    a first electrode;
    a second electrode spaced from the first electrode;
    a controller operably coupled to the first electrode and the second electrode;
    a housing that is configured for subcutaneous, submuscular or substernal deployment, the housing having a first major housing side extending substantially parallel with an opposing second major housing side and a minor side wall extending therebetween;
    the first electrode including a first electrode portion disposed on the first major housing side and a second electrode portion disposed on the opposing second major housing side;
    the second electrode including a first electrode portion disposed on the first major housing side and a second electrode portion disposed on the opposing second major housing side;
    the controller configured to selectively electrically couple to either the first electrode portion of the first electrode or the second electrode portion of the first electrode and to selectively electrically couple to either the first electrode portion of the second electrode or the second electrode portion of the second electrode; and
    the controller configured to communicate information about the cardiac activity to a second medical device.

* * * * *